(12) United States Patent
Møller

(10) Patent No.: US 12,274,858 B2
(45) Date of Patent: Apr. 15, 2025

(54) WEARABLE INJECTION DEVICE

(71) Applicant: TJCC ApS, Viby Sj (DK)

(72) Inventor: Claus Schmidt Møller, Fredensborg (DK)

(73) Assignee: TJCC ApS, Viby Sj (DK)

( * ) Notice: Subject to any disclaimer, the term of this patent is extended or adjusted under 35 U.S.C. 154(b) by 680 days.

(21) Appl. No.: 17/002,335

(22) Filed: Aug. 25, 2020

(65) Prior Publication Data

US 2020/0384195 A1 Dec. 10, 2020

Related U.S. Application Data

(62) Division of application No. 16/070,773, filed as application No. PCT/DK2017/050011 on Jan. 20, 2017, now Pat. No. 11,229,738.

(30) Foreign Application Priority Data

| Jan. 28, 2016 | (DK) | PA 2016 00060 |
| Mar. 2, 2016 | (DK) | PA 2016 00134 |
| Jun. 23, 2016 | (DK) | PA 2016 00372 |
| Oct. 3, 2016 | (DK) | PA 2016 00585 |

(51) Int. Cl.
*A61M 5/142* (2006.01)
*A61M 5/145* (2006.01)
*A61M 5/24* (2006.01)
*A61M 5/158* (2006.01)

(52) U.S. Cl.
CPC .... *A61M 5/14248* (2013.01); *A61M 5/14244* (2013.01); *A61M 5/14526* (2013.01); *A61M 5/2429* (2013.01); *A61M 5/2455* (2013.01); *A61M 5/2466* (2013.01); *A61M 2005/14252* (2013.01); *A61M 2005/14513* (2013.01);
(Continued)

(58) Field of Classification Search
CPC .......... A61M 5/14244; A61M 5/14526; A61M 5/1452; A61M 5/2429; A61M 5/2466; A61M 5/2455; A61M 5/14248; A61M 2005/14513; A61M 2005/1585; A61M 2005/2474; A61M 2005/14252; A61M 2005/1581
See application file for complete search history.

(56) References Cited

U.S. PATENT DOCUMENTS

| 5,169,390 A | 12/1992 | Athayde et al. |
| 2005/0182391 A1 | 8/2005 | Schiltges et al. |
| 2007/0073228 A1 | 3/2007 | Mernoe et al. |

(Continued)

FOREIGN PATENT DOCUMENTS

| CN | 1874809 A | 12/2006 |
| CN | 104379192 A | 2/2015 |

(Continued)

OTHER PUBLICATIONS

International Search Report and Written Opinion from corresponding International Application No. PCT/DK2017/050011, mailed Jul. 10, 2017; 16 pages.

*Primary Examiner* — Scott J Medway
*Assistant Examiner* — Anh Bui
(74) *Attorney, Agent, or Firm* — Tucker Ellis LLP

(57) ABSTRACT

A wearable injection device for subcutaneous injection of a therapeutic agent, wherein the dose is injected over a specified period of time after the device is activated.

1 Claim, 16 Drawing Sheets

Figure 1:
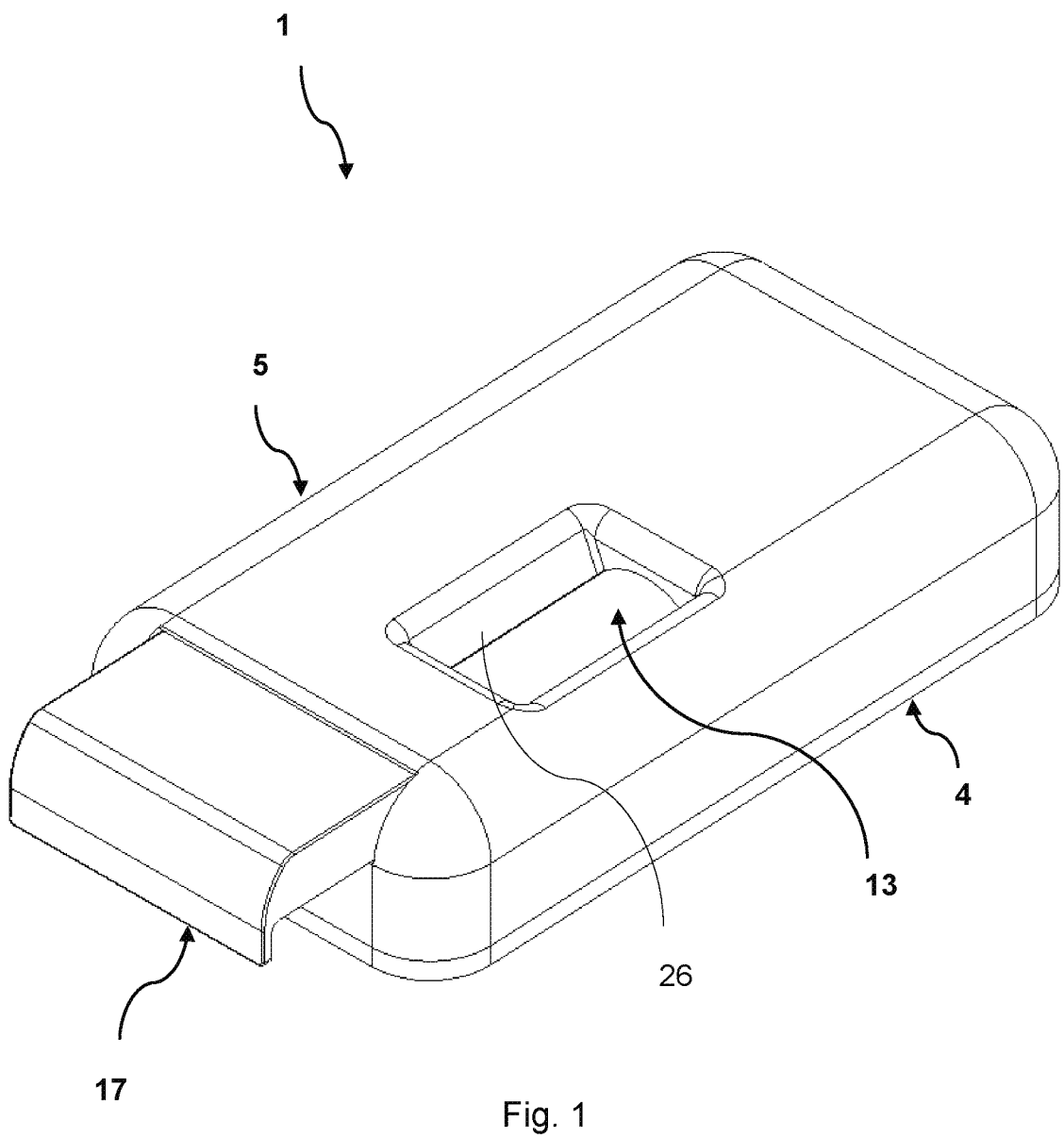

(52) U.S. Cl.
CPC ............... *A61M 2005/1585* (2013.01); *A61M 2005/2474* (2013.01)

(56) References Cited

U.S. PATENT DOCUMENTS

| | | | |
|---|---|---|---|
| 2008/0009805 A1 | 1/2008 | Ethelfeld | |
| 2011/0306929 A1* | 12/2011 | Levesque | A61M 5/14248 604/150 |
| 2013/0218093 A1 | 8/2013 | Markussen et al. | |
| 2014/0148784 A1* | 5/2014 | Anderson | A61M 5/14248 604/150 |
| 2017/0189609 A1 | 7/2017 | Wei | |

FOREIGN PATENT DOCUMENTS

| | | |
|---|---|---|
| DE | 4106624 A1 | 9/1992 |
| EP | 2060286 A1 | 5/2009 |
| EP | 2179754 A1 | 4/2010 |
| WO | 2004009162 A1 | 1/2004 |
| WO | 2004011062 A1 | 2/2004 |
| WO | 2004098684 A2 | 11/2004 |
| WO | 2008142394 A1 | 11/2008 |
| WO | 2011054755 A1 | 5/2011 |
| WO | 2012145752 A2 | 10/2012 |
| WO | 2015199981 A1 | 12/2015 |

\* cited by examiner

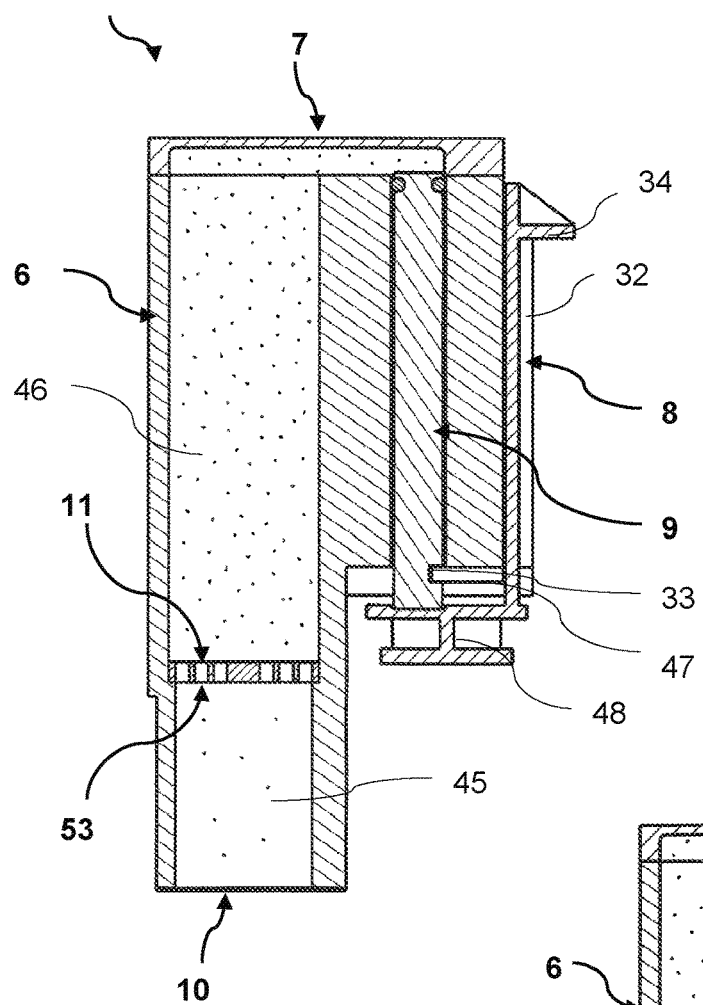
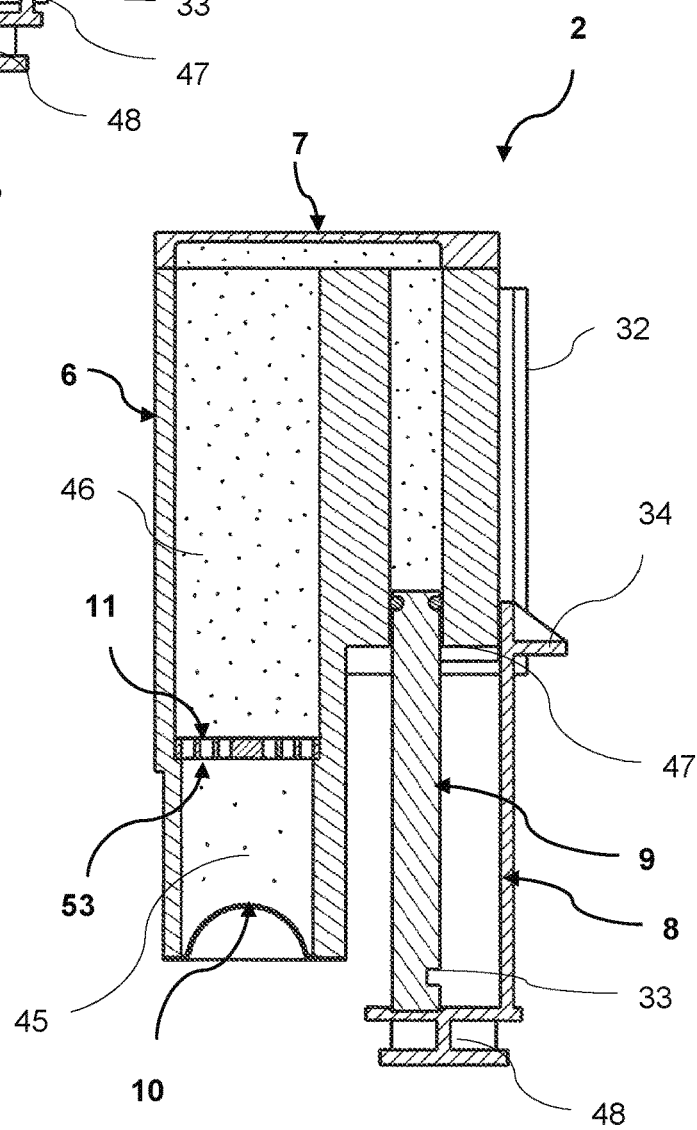

WEARABLE INJECTION DEVICE

RELATED APPLICATION DATA

This application is a divisional application of U.S. application Ser. No. 16/070,773. filed Jul. 17, 2018, which is a national phase of International Application No. PCT/DK2017/050011, filed Jan. 20, 2017, which claims the benefit of Denmark Application Nos. PA 2016 00060, filed Jan. 28, 2016, PA 2016 00134, filed Mar. 2, 2016, PA 2016 00372, filed Jun. 23, 2016, and PA 2016 00585, filed Oct. 3, 2016, all of which are incorporated herein by reference in their entireties.

FIELD OF INVENTION

The invention relates to a wearable injection device for subcutaneous injection of a therapeutic agent, wherein the dose is injected over a specified period of time.

BACKGROUND

During the recent years, self-injection of various therapeutic agents by means of auto injectors on a daily, weekly, monthly or just on a one-time basis has become more common. As the effect of a therapeutically effect of a therapeutic agent can be slowed down to last longer, it is often an advantage and more convenient for the patient to inject fairly large doses of the therapeutic agent and thereby to inject himself less often. However, for most state of the art auto injectors on the market today the maximum injectable dose is one to two millilitres and, more important, doses above two millilitres may cause pain or back flow of the therapeutic agent and cannot be recommended. Thus, there is a need for other solutions for injecting large volumes of therapeutic agent, and injectors for being attached to the body and worn for a specified time such as e.g. an hour provides a convenient solution to the problem.

DESCRIPTION OF THE RELATED ART

US2007073228 describes an infusion pump device comprising a drive system that incrementally dispenses fluid from the pump device in a controlled manner. The drive system includes a rotational motor that is coupled to a string member, which is used to adjust a pawl relative to a ratchet body in certain specified intervals. The ratchet body is coupled to a driving part such as a worm gear, which drives an incremental screw to push a plunger in a cartridge forward. This device is based on rather expensive mechanical and electronically parts and seems to be rather complicated and indeed not suitable for a disposable device. Furthermore, the device includes some delicate parts such as a very thin wire, which is winded and un-winded a large number of times.

WO2008142394 describes a drive mechanism for a therapeutic agent delivery pump wherein a tensed spring urges a plunger in a cartridge to press therapeutic agent out through a needle. A regulating mechanism based on an electrically stepper motor and a gear is holding back the plunger so that only a specified rate of the plunger is allowed. Also, this mechanism seems to be very expensive and is not suited for use in a disposable device.

In both DE4106624 and WO2004011062, simple devices for administering an injectable product using an osmotic drive are described. The devices comprise a housing provided with a first chamber containing a solvent, a second chamber containing a solution, and a product chamber containing the product. A semi-permeable forward osmosis membrane is arranged between the first chamber and the second chamber. Either a plunger in connection with the second chamber or the solution itself is driving a plunger in the product chamber. A triggering device for triggering the osmotic drive comprises an impermeable foil located between the first chamber and the second chamber, which must be pierced to trigger the device. These devices seem to have a few shortcomings such as e.g. vacuum being induced in the first chamber and a fast decreasing osmotic force due to the size and arrangement of the chambers.

In WO2004098684, a device attachable to the skin of a user is described. Before use and during mounting of the device, it is handled via an insertion device comprising two prolonged section. When the user squeezes these two sections against each other, a blade spring is tensed and, at a certain point, the spring releases the force pushing a double-ended and bended needle into the skin of the user and through a septum on a flexible reservoir at the same time. Hereafter the insertion device is removed. When the injection is fulfilled, the device is removed and the needle at the same time retracted from the skin of the user. Though the insertion method is very well described it is unclear how the needle should be removed from the skin again if not just by removing the entire device. Another disadvantage is that the needle is not encapsulated so that it can be sterilized separately, but the entire device must be sterilized.

BRIEF DESCRIPTION OF THE INVENTION

It is a first objective of the invention to provide a wearable injection device based on an osmotic engine, which is small, cheap to manufacture and which is capable of accommodating large injections over a controlled period of time.

It is a second objective of the invention to provide a needle system for a wearable injection device, which is simple, which can be sterilized separately, and which accommodates both insertion and retraction of the needle.

The first objective of the invention can be obtained by a wearable injector comprising an osmotic actuator, a cartridge filled with the therapeutic agent to be injected and with a plunger to be moved by the osmotic actuator after the device has been activated, and a fully enclosed needle assembly with sterile barriers. The osmotic actuator comprises a plunger movable by the pressure in the actuator and in contact with the plunger in the cartridge. The trigger mechanism comprises a protrusion, which during the triggering operation cooperates with a needle assembly in moving the needle to an exposed position and creating a fluid communication between the cartridge and the injection site.

After the device is triggered and the needle is moved to the exposed position and the osmotic actuator has started to build up pressure, the plunger in the osmotic actuator pushes on the plunger in the cartridge, and the therapeutic agent flows from the cartridge through the inserted needle and in to the injection site. The needle may be functionally connected with a soft cannula to increase convenience, and arranged in such a way that the fluid communication between the cartridge and the injection site is through the soft cannula. In this scenario, the needle is only used for penetration at the injection site.

The needle is locked in the activated position by a needle lock, and at the end of the injection, the plunger in the osmotic actuator pushes the needle lock out of engagement with the needle assembly and the needle is retracted to a hidden position inside the device.

Thus, the present invention relates to a wearable injection device adapted to be placed on the body of a user and to perform a subcutaneous injection at an injection site on the skin of the user over some time after activation of the device, comprising a base plate for interfacing the skin of the user,
an osmotic actuator,
a trigger button to initiate the injection,
a cartridge containing a therapeutic agent,
a needle with a sharpened end, and wherein, when the device is activated by pushing the trigger button, the sharpened end of the needle is inserted at the injection site through an opening in the base plate, and wherein fluid communication between the injection site and the cartridge is established simultaneous with or after the insertion of the sharpened end of the needle at the injection site.

In another embodiment of the invention, the wearable injection device further comprises at least one plunger, which is movable by means of osmotic pressure in the osmotic actuator and arranged to cause the fluid communication between the injection site and the cartridge to be disconnected when the plunger has reached a specified position.

By letting the position of the movable plunger define when the needle is retracted an additional sensor is avoided and the time of retraction can be defined very precisely.

In yet another embodiment of the invention, the fluid communication is establish through the hollow needle.

This makes it possible to make a very simple fluid communication.

In yet another embodiment of the invention, the needle is retracted from the injection site before the injection starts and the fluid communication is established by means of a soft cannula, which is inserted together with the needle.

This is a more complicated solution, which in turns offers a high degree of convenience for the user, as a soft cannula cannot be sensed even if the user is very active.

In yet another embodiment of the invention, the sharpened end of the needle, at least during the majority of the injection, is locked in the inserted position by means of a needle lock, and, at the end of the injection, is moved a distance by the plunger whereby the sharpened end of the needle is set free and retracted to an inaccessible position by means of a spring.

This provides a very simple way to control when the needle should be inserted and when it should be retracted.

In yet another embodiment of the invention, the sharpened end of the needle is set free and retracted to an inaccessible position during the final part of the injection and the therapeutic agent expelled from the cartridge hereafter is collected inside the device.

By retracting the needle during injection, it is possible to use the movement of plunger in the actuator or another movable element to push the needle lock and release the needle.

In yet another embodiment of the invention, a telescopically unit is transmitting the pressure from the actuator to the plunger.

This makes it possible to reduce the needed amount of fluid in the actuator by making a ratio between the diameter of the telescopically unit and the diameter of the cartridge.

In yet another embodiment of the invention, the osmotic actuator comprises a low-pressure chamber containing a solution,
a high-pressure chamber containing a solution,
an activation chamber containing a solvent, and
a forward osmosis membrane, the activation chamber and the low-pressure chamber are separated by a barrier and the high-pressure chamber and the low-pressure chamber are separated by the forward osmosis membrane, the volumes of both low-pressure chamber and high-pressure chamber are expandable and a plunger is moved proportionally with the expansion of the high-pressure chamber, and a pressure large enough to move the solvent through the barrier and into the low-pressure chamber is induced in the activation chamber during activation of the actuator.

This provides a simple osmotic actuator, in which the osmotic membrane is wetted and in balance with a solution on both side of the membrane until the solvent is forced into the low-pressure chamber.

In yet another embodiment of the invention, the osmotic actuator comprises a low-pressure chamber containing a solvent,
a high-pressure chamber containing a solvent,
an activation chamber containing salt crystals and/or a solution, and
a forward osmosis membrane, the low- and high-pressure chambers are separated by the forward osmosis membrane, the high-pressure chamber and the activation chamber are separated by a barrier, the high-pressure chamber is expandable and a plunger is moved proportionally with the expansion of the high-pressure chamber, and the contents of the activation chamber and the high-pressure chamber are mixed during activation of the actuator.

By having a solvent on each side of the osmosis membrane and salt crystals or a salt solution in the activation chamber and by letting the activation chamber open into the pressure chamber, it is easier to provide an oversaturated solution in the pressure chamber to avoid dilution and to avoid that the osmotic pressure gets lower during the injection.

In yet another embodiment of the invention, the barrier is a one-way valve.

This provides a tight barrier with a relatively low breakthrough force.

In yet another embodiment of the invention, the barrier is a membrane that breaks when the pressure in the activation chamber reaches a certain level.

This solution requires a higher-break through force, but provides a very little resistance when the membrane is penetrated.

In yet another embodiment of the invention, the barrier is a movable shield.

By moving a cylindrically shield, e.g. tightened with O-rings, the break-through force and, thereby, the trigger force can be very low and it is avoided that remains from a foil can cause problems within the actuator.

In yet another embodiment of the invention, the barrier is a capsule, which can be broken, or a bag, which can be cut into pieces.

In yet another embodiment of the invention, the forward osmosis membrane is a planar flat-sheet membrane.

Due to the structure of a wearable injection device, a flat-sheet membrane can have a rather big area and in many cases this will be sufficient to build up the pressure in the actuator.

In yet another embodiment of the invention, the total area of the forward osmosis membrane is composed by one or more planar but not parallel flat-sheet membranes.

This is an alternative way to provide a bigger area if one flat-sheet membrane is not enough.

In yet another embodiment of the invention, the total area of the forward osmosis membrane is composed by one or more non-planar osmotic membranes.

This is an alternative way to provide a bigger area if one flat-sheet membrane is not enough.

In yet another embodiment of the invention, the total area of the forward osmosis membrane is composed by one or more hollow osmotic membranes with a cylindrical cross-section.

This is very efficient when the actuator must work very fast or if it should be used as a platform, as it is very easy to vary the speed by varying the number of membranes or the length and/or diameter of the membrane or membranes.

In yet another embodiment of the invention, a passage between the high- and low-pressure chambers opens when the pressure in the high-pressure chamber reaches a certain level.

This prevents that a pressure will build up when the plunger in the cartridge has been moved to the end position.

In yet another embodiment of the invention, an acoustic and/or tactile and/or visual signal is mechanically generated by an item moved by the pressure difference between the high- and low-pressure chambers when the passage opens.

In this way, the device can indicate to the user in a very inexpensive way that the injection has been fulfilled.

In another aspect of the invention, it relates to a wearable injection device is comprising a cartridge with a septum and a movable plunger and containing a therapeutic agent to be injected, and a needle assembly, the needle assembly further comprising:
- a first part with a needle being adapted to penetrate an injection site on the skin of a user and being movable in a direction mainly perpendicular to the axis of the cartridge,
- a second part with a portion being adapted to penetrate the septum of the cartridge and being movable in a direction mainly parallel to the axis of the cartridge, and
- a spring maintaining the first part in an initial position, wherein the needle of the first part in the initial position is hidden within the wearable injection device, wherein, during activation of the device, the first part with the needle is moved against the biasing of the spring to penetrate the injection site and the second part is moved to penetrate the septum of the cartridge and to lock the first part in the inserted position, and wherein a fluid communication between the first part and the second part is established simultaneous with or after the locking of the first part in the inserted position.

The fact that there is no fluid communication between the first and the second parts before the device is activated eliminates the need for a flexible connection between the needle for penetrating the septum on the cartridge and the needle for piercing the skin of the user, and at the same time it makes it easier to sterilize the needle assembly by means of steam.

In another embodiment of the invention, the second part is moved by the movable plunger near the end of the injection, whereby the first part is released and moved back to a hidden position inside the device by the spring.

By letting the plunger in the cartridge release the needle, the release mechanism can be very simple and the time for interrupting the injection can be very precise.

In yet another embodiment of the invention, electronic means for indicating and/or transmitting an operational status of the device are provided.

This makes it possible for e.g. health care staff to be informed of and follow the medicating status of the user.

FIGURES

Figure 2:
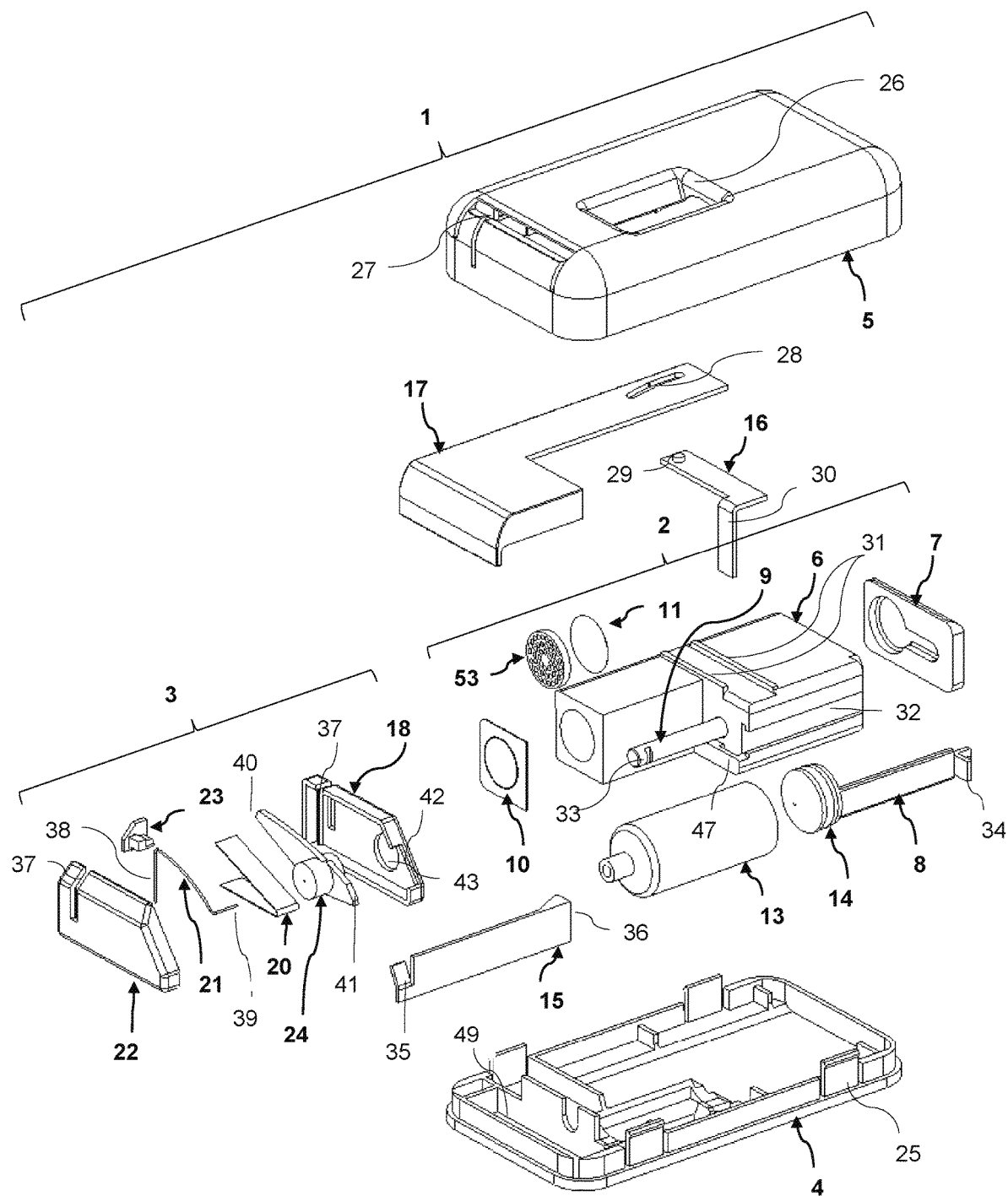
Figure 3:
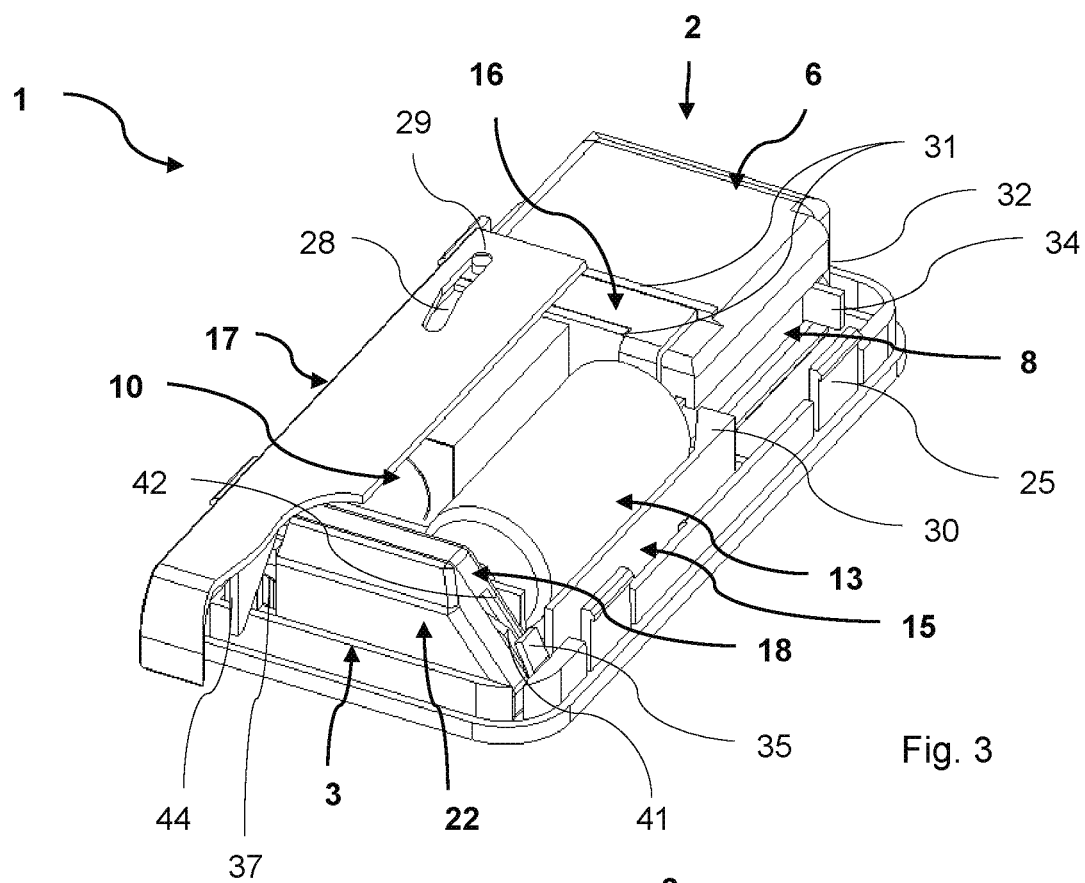
Figure 4:
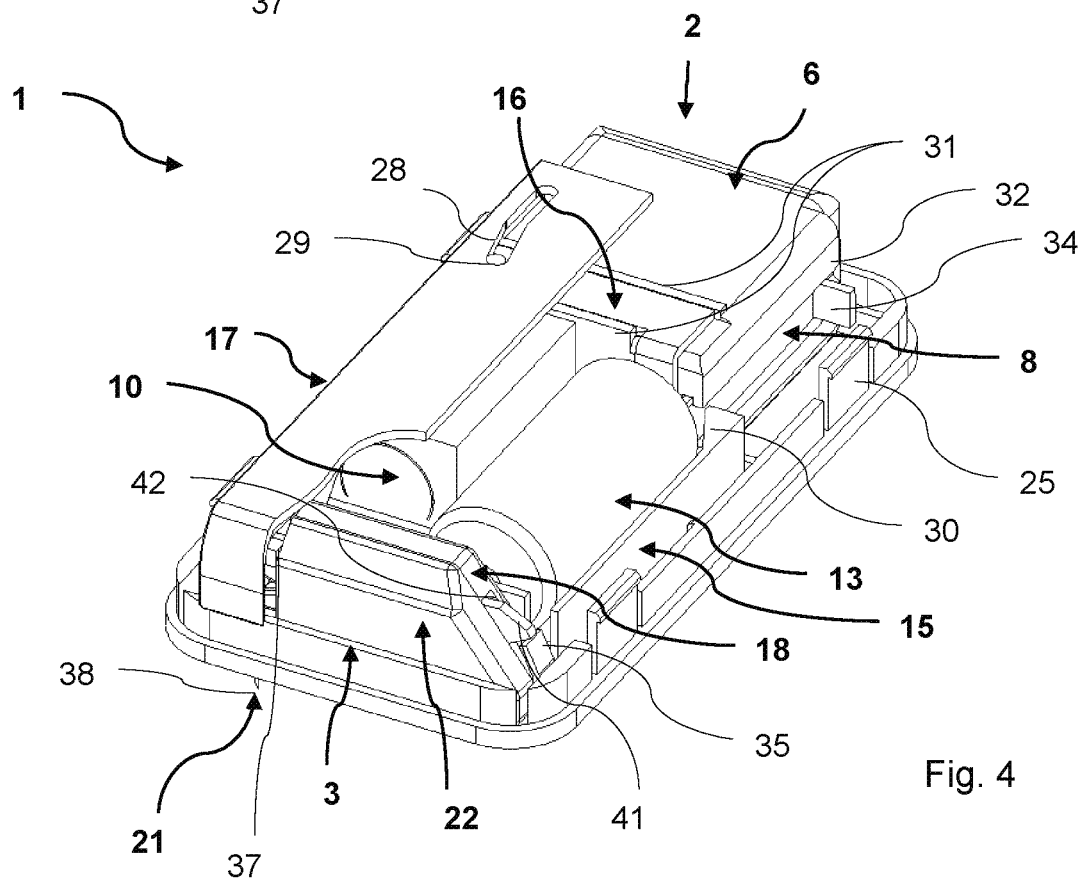
Figure 5:
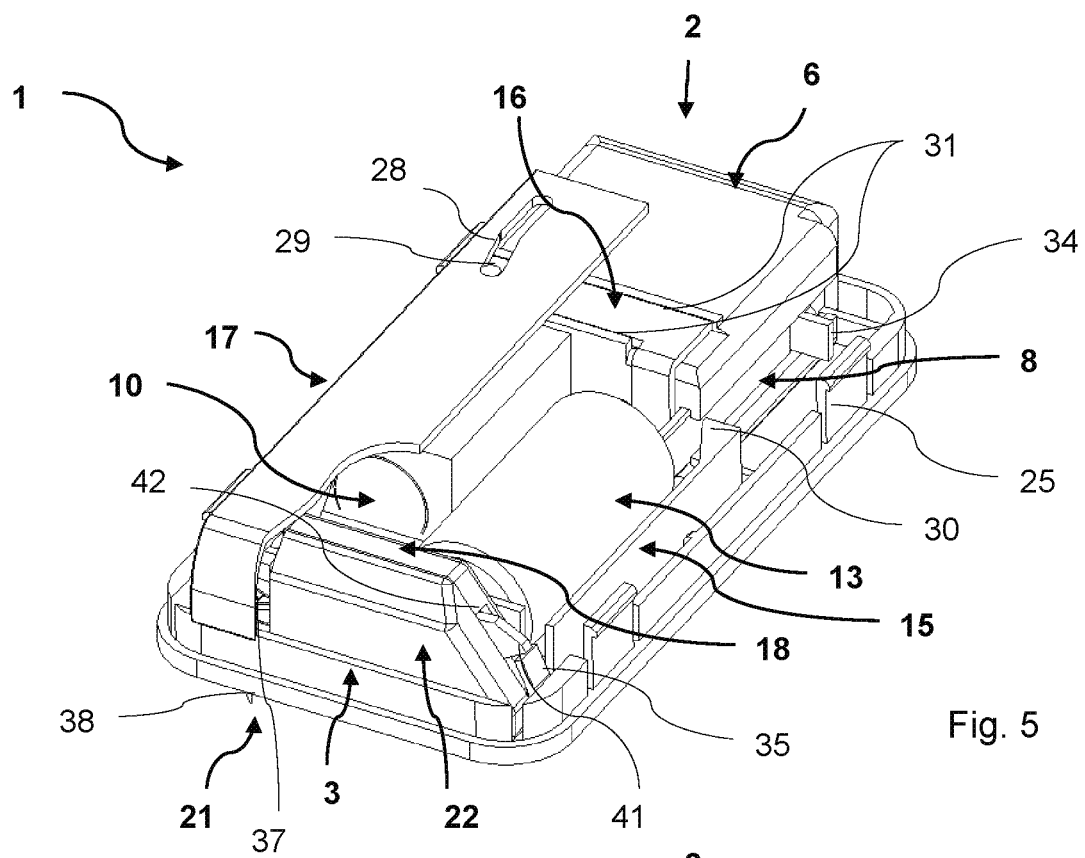
Figure 6:
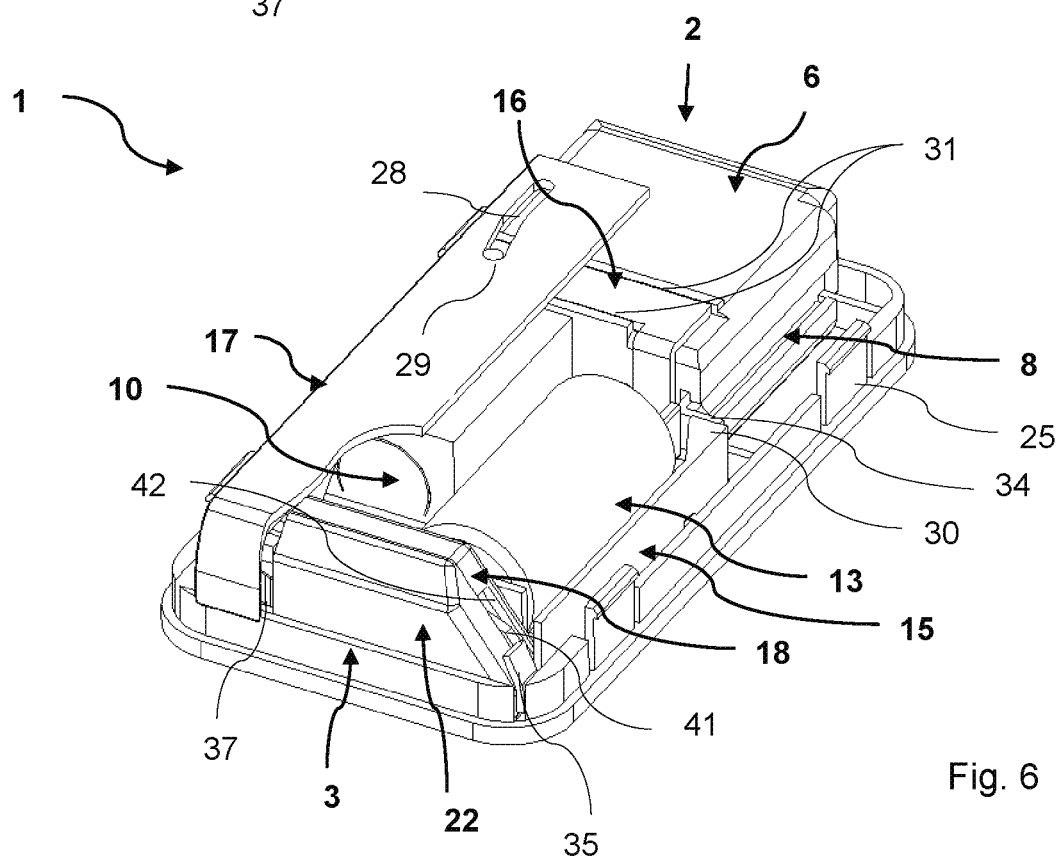
Figure 7:
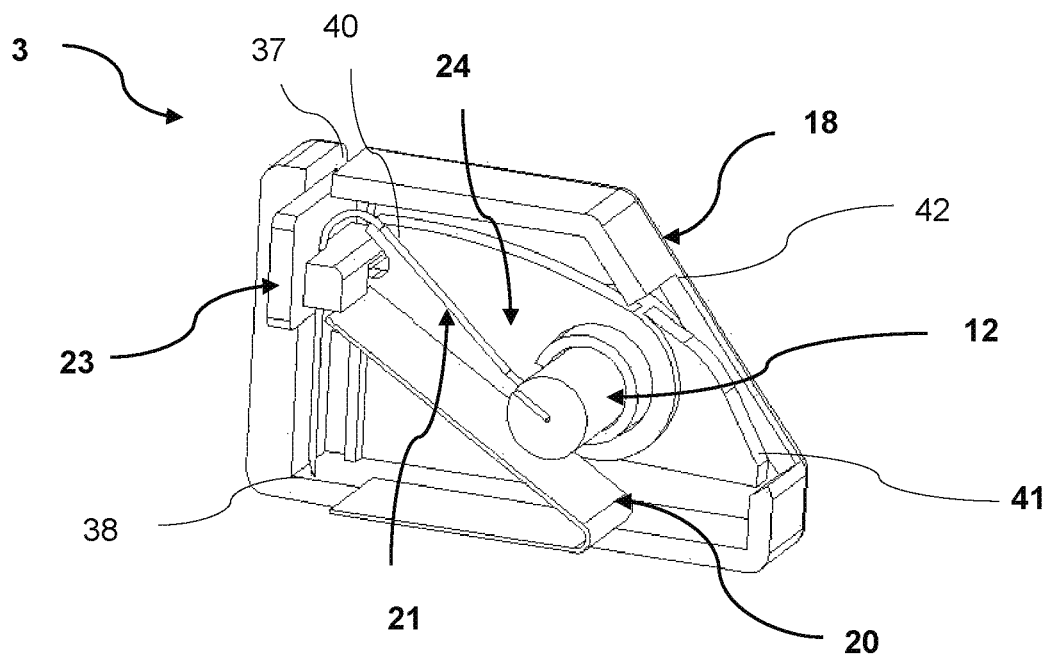
Figure 8:
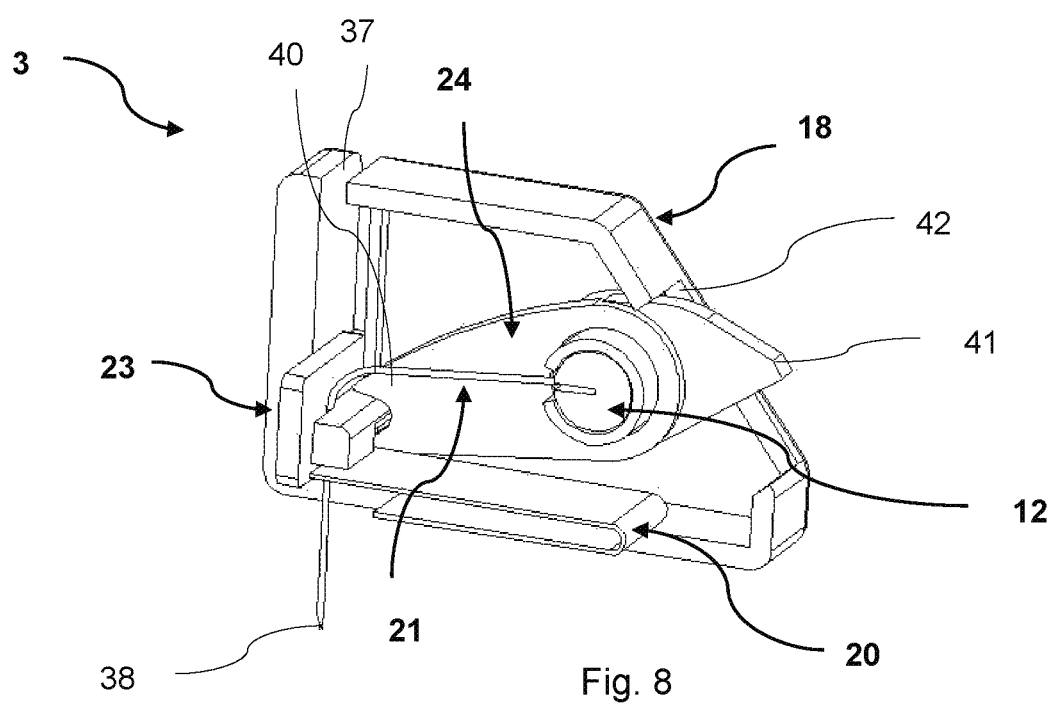
Figure 11:
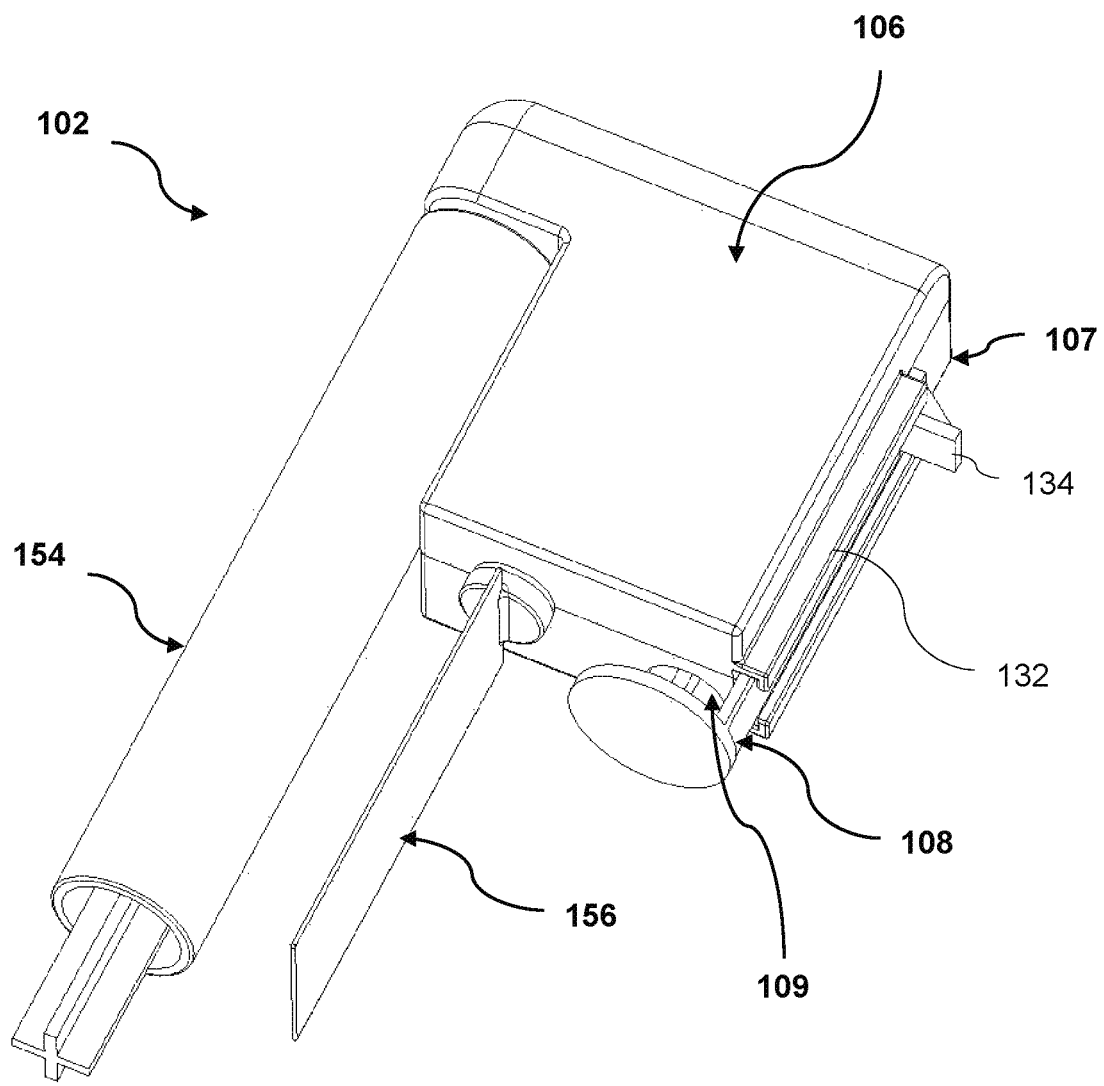
Figures 12, 13:
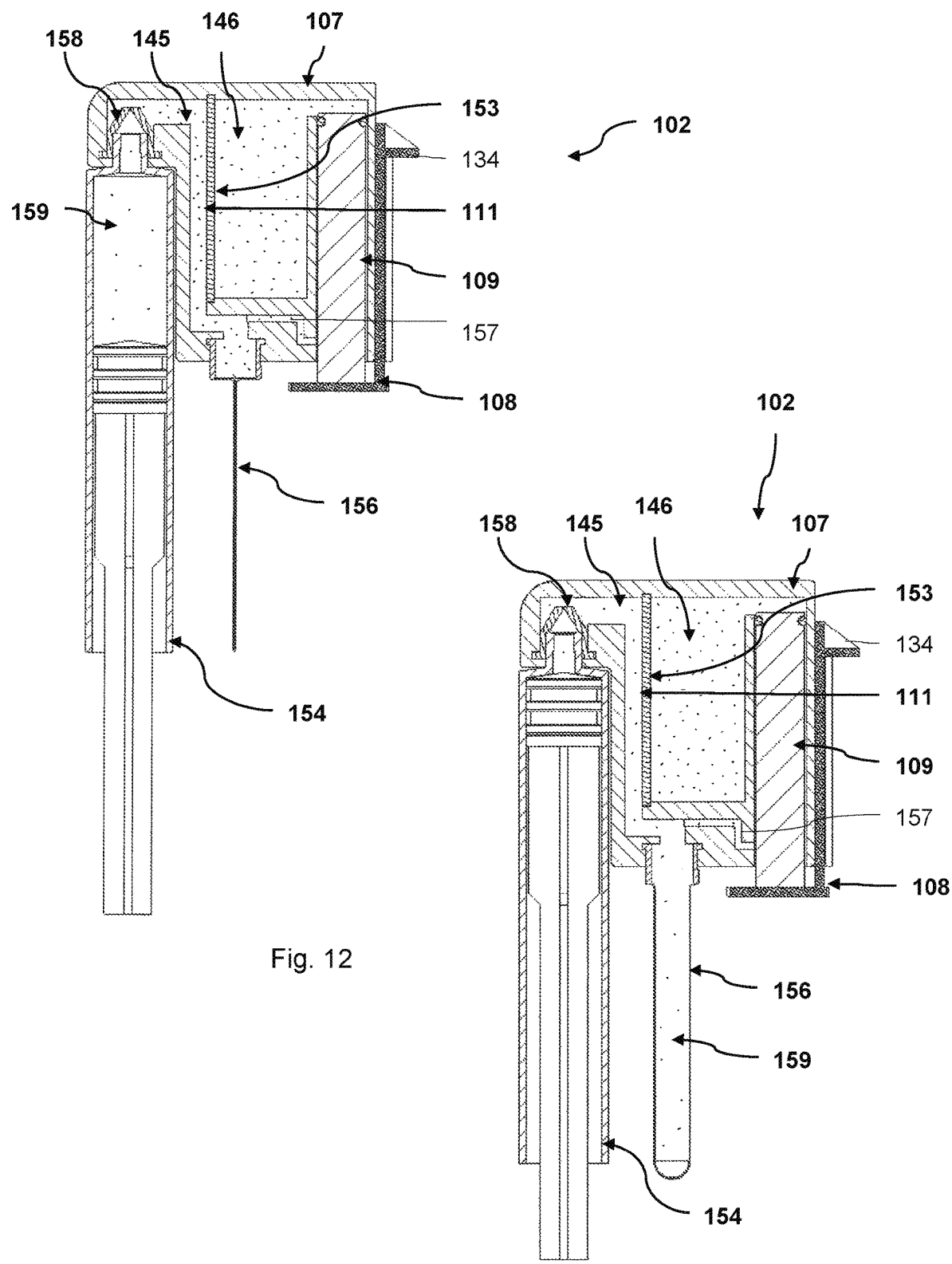
Figure 14:
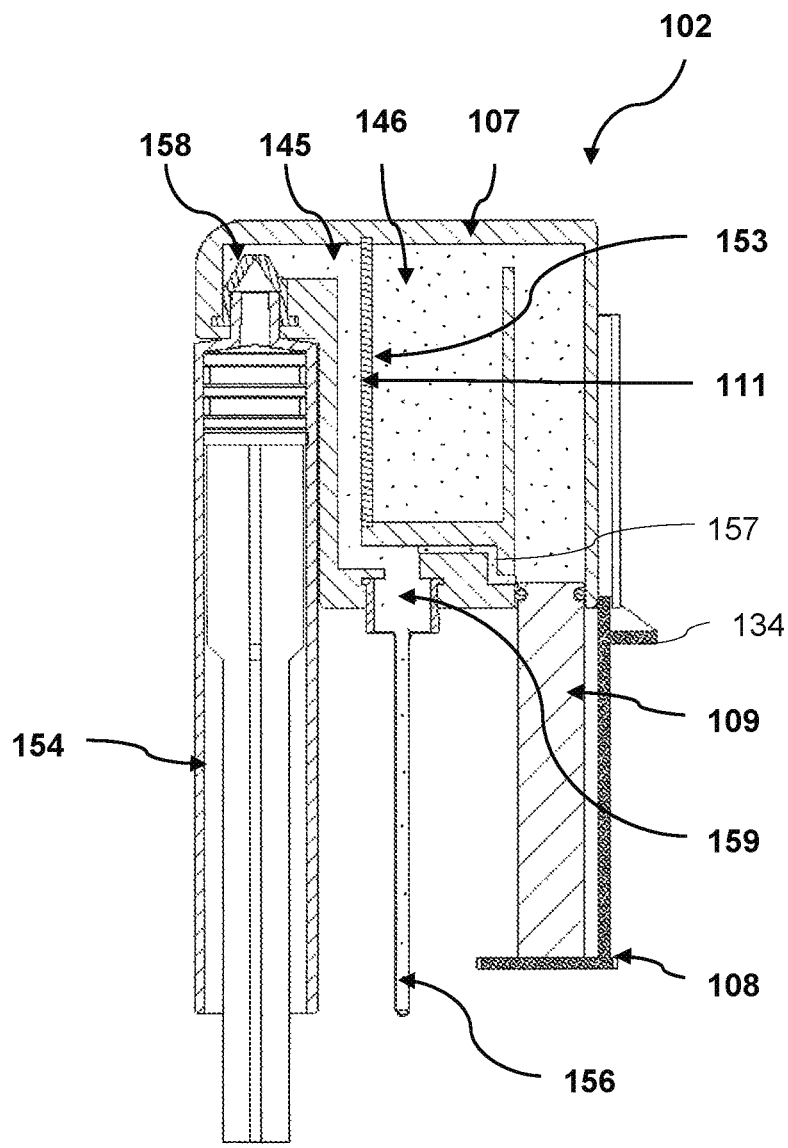
Figure 15:
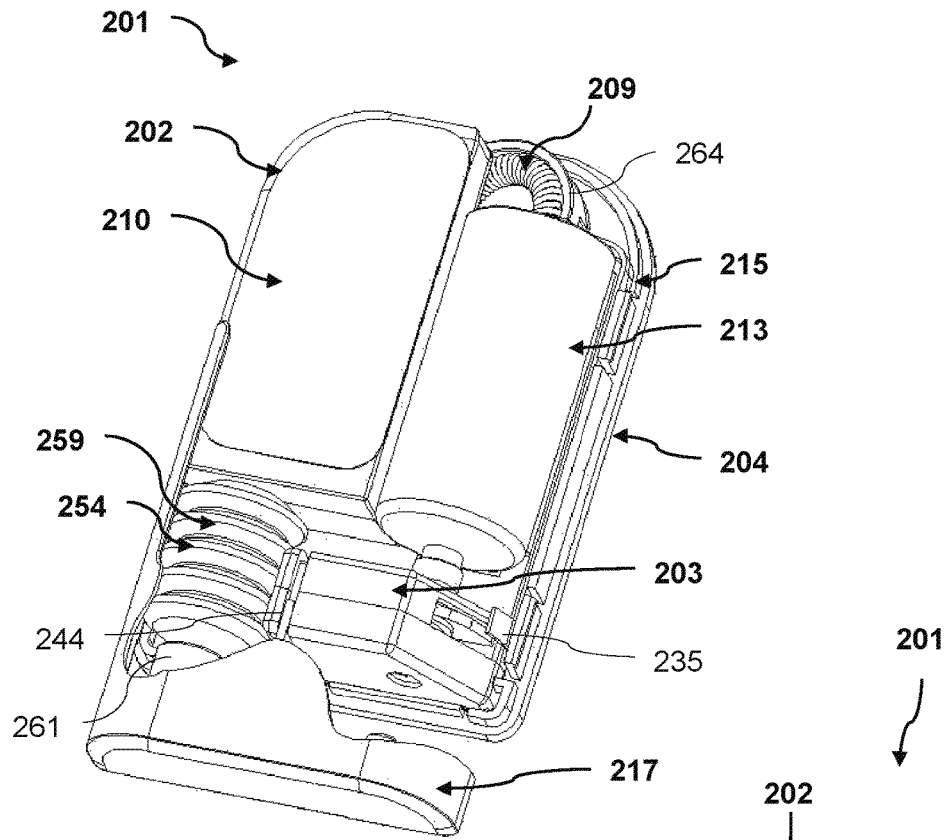
Figure 16:
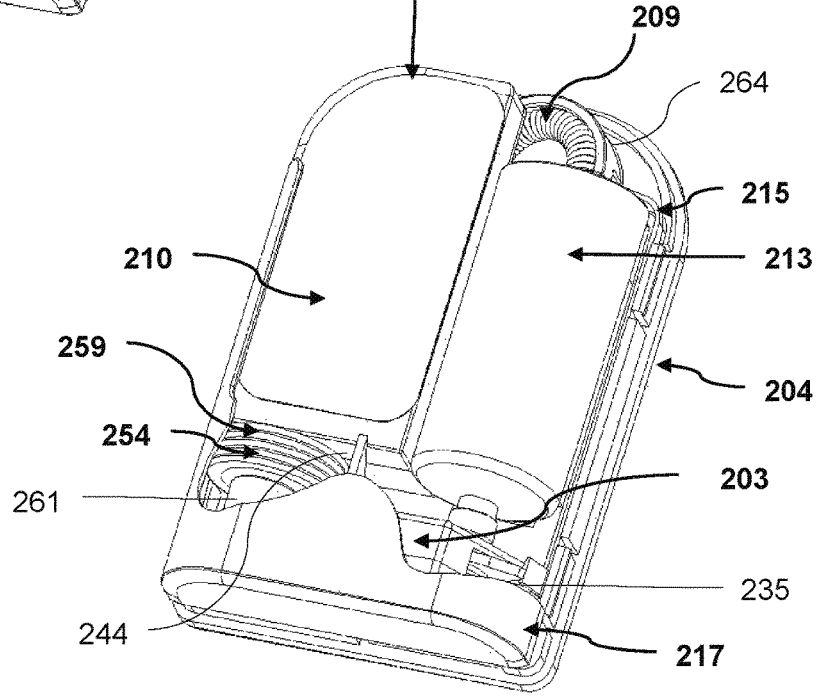
Figure 17:
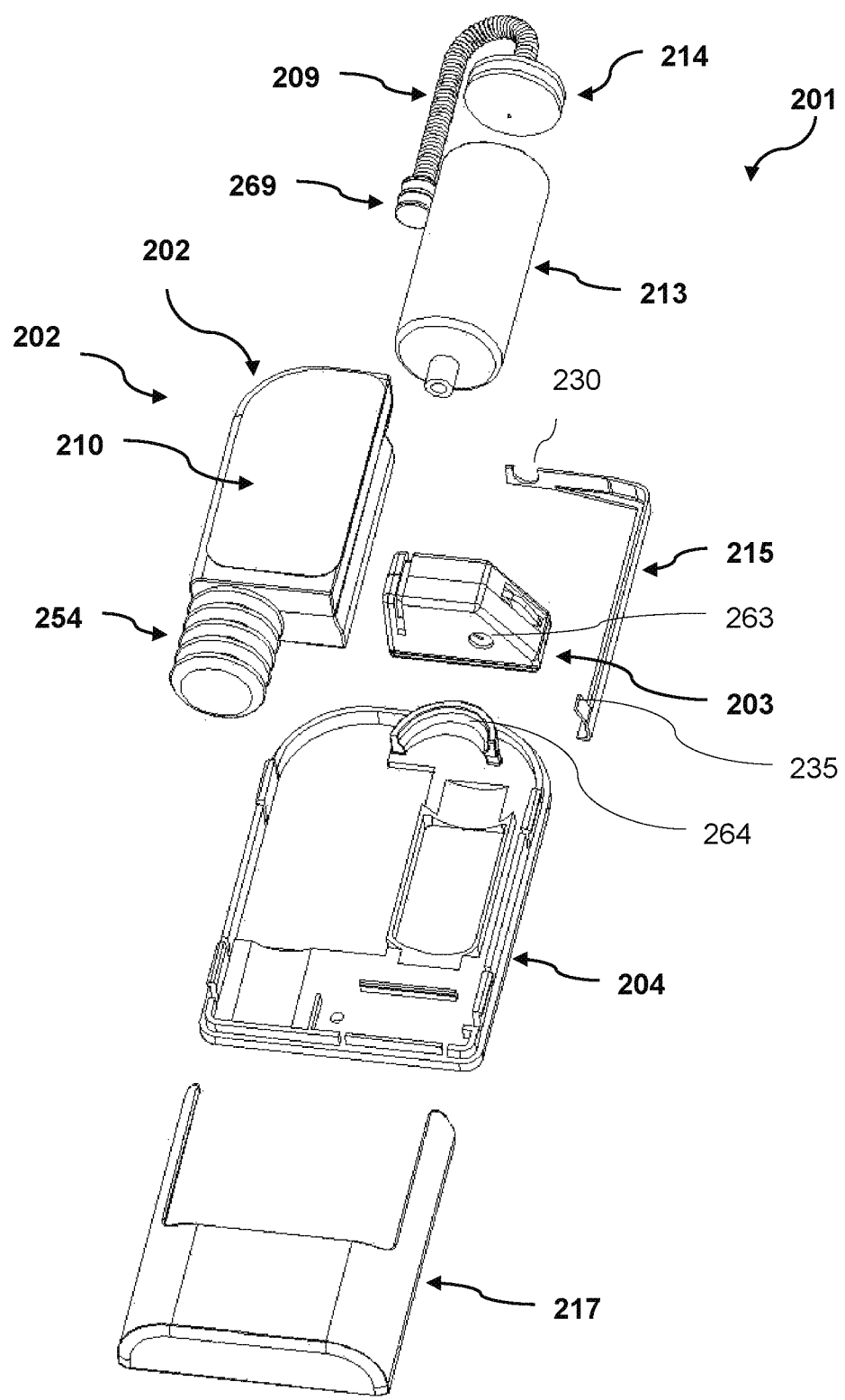
Figure 18:
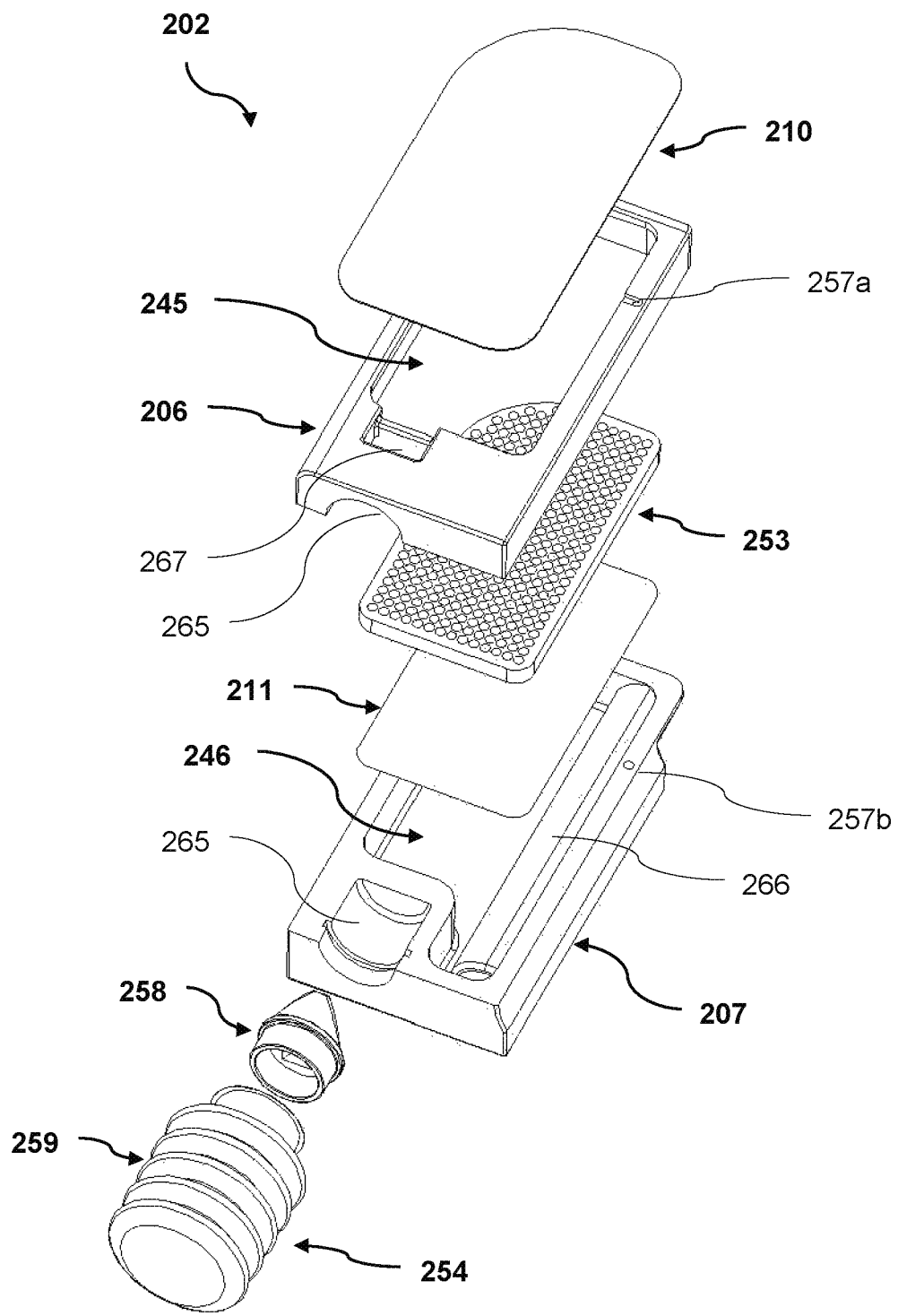
Figure 19:
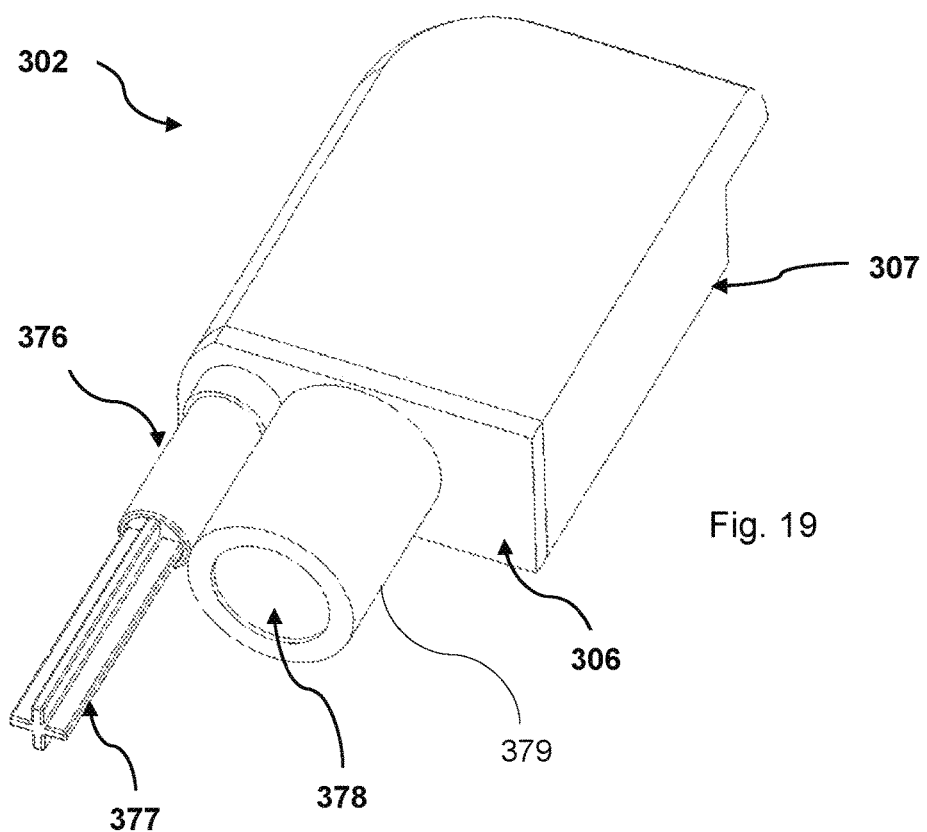
Figure 20:
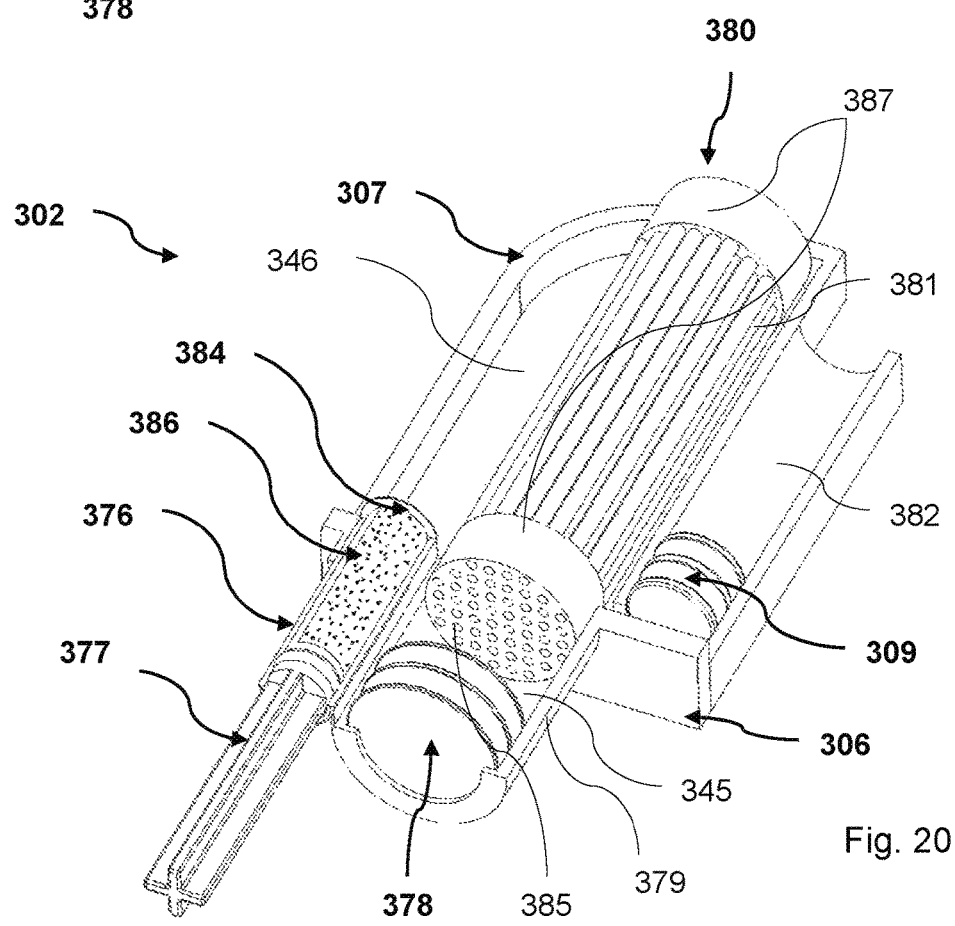
Figure 21:
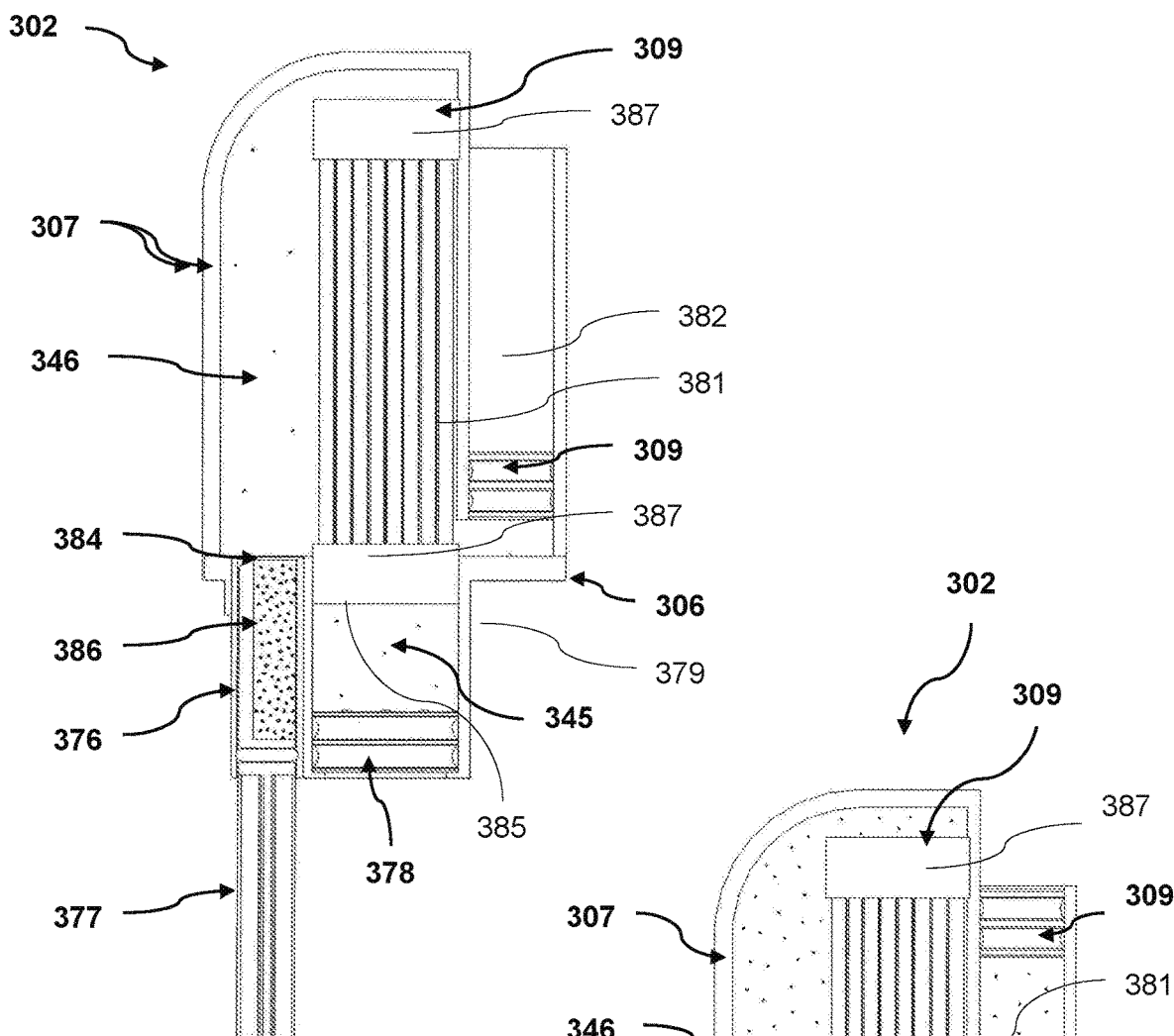
Figure 22:
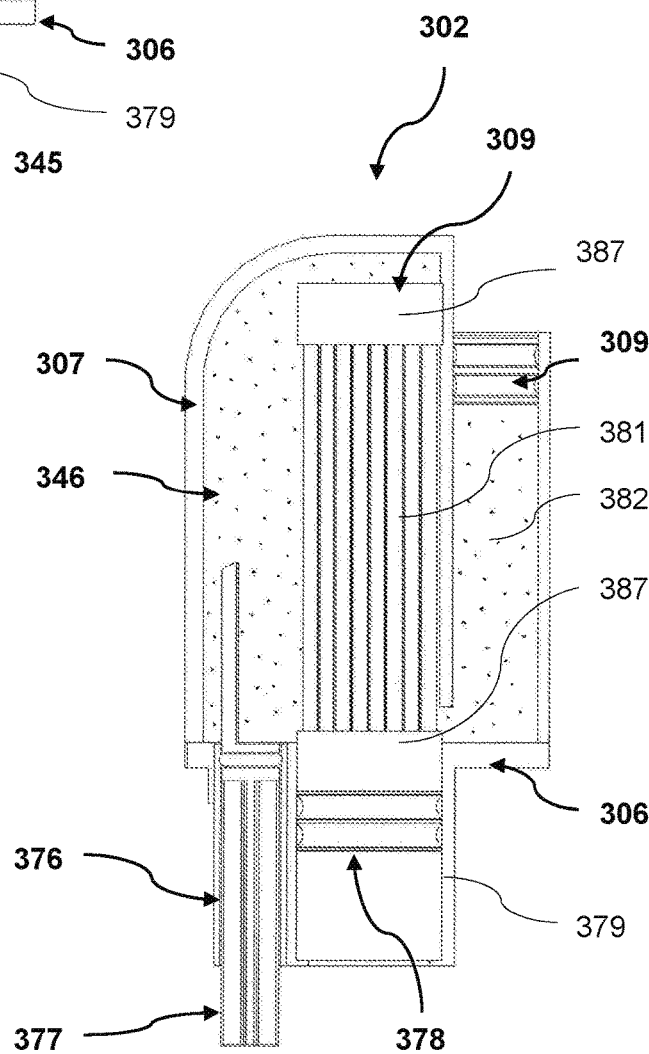
Figure 23:
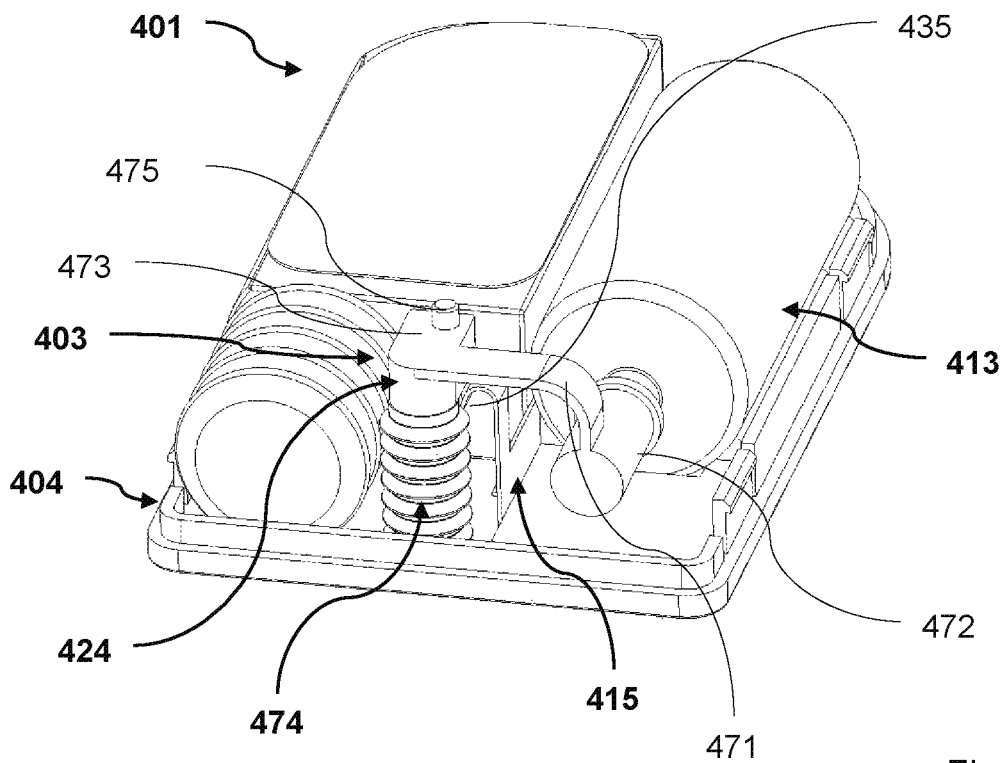
Figure 24:
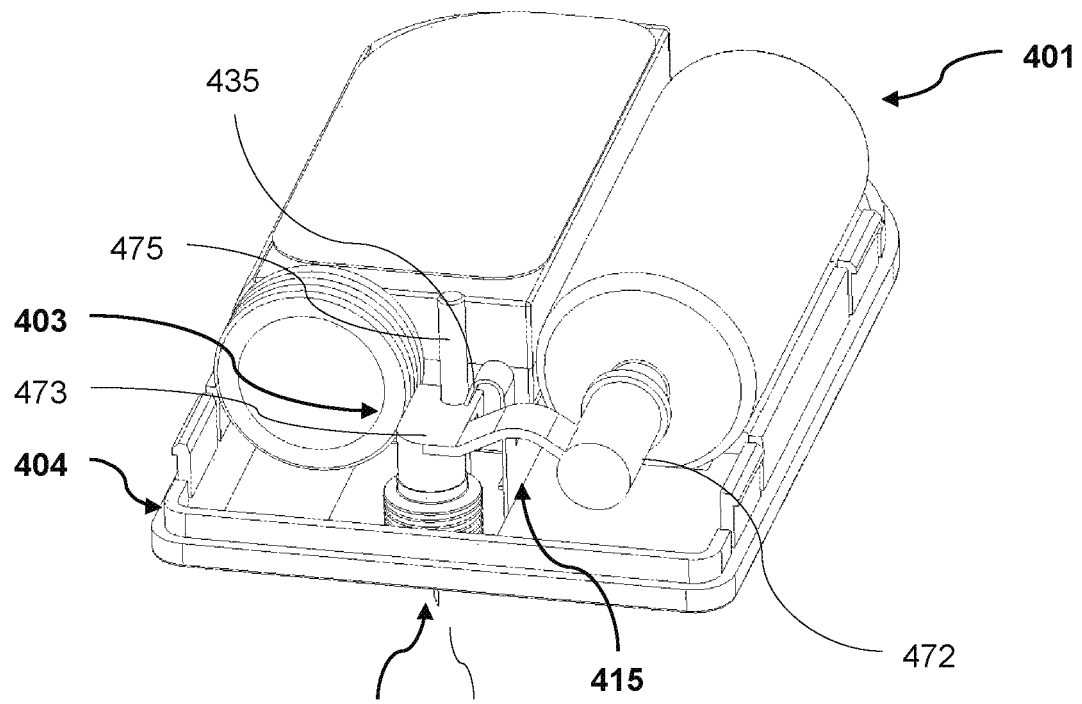
Figure 25:
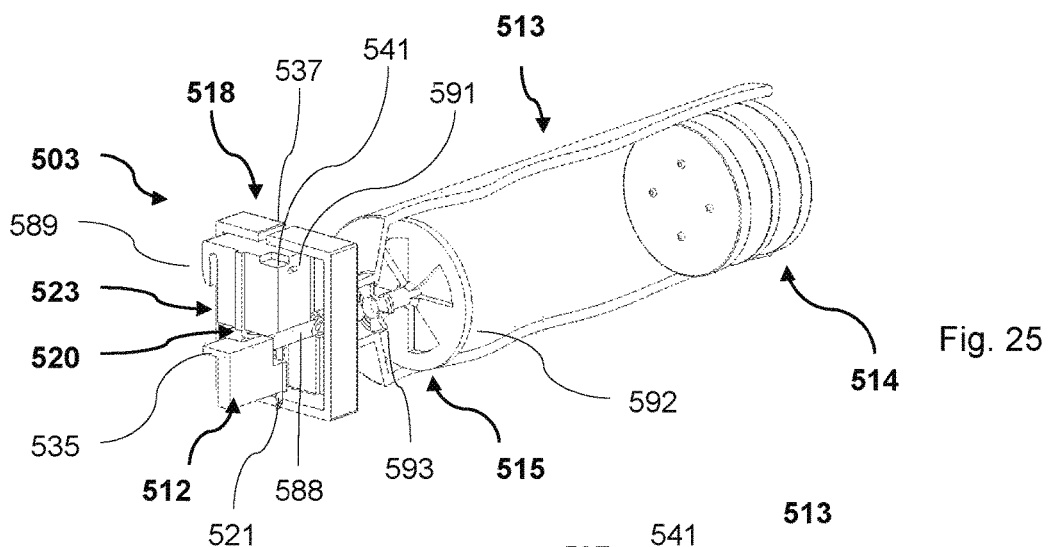
Figure 26:
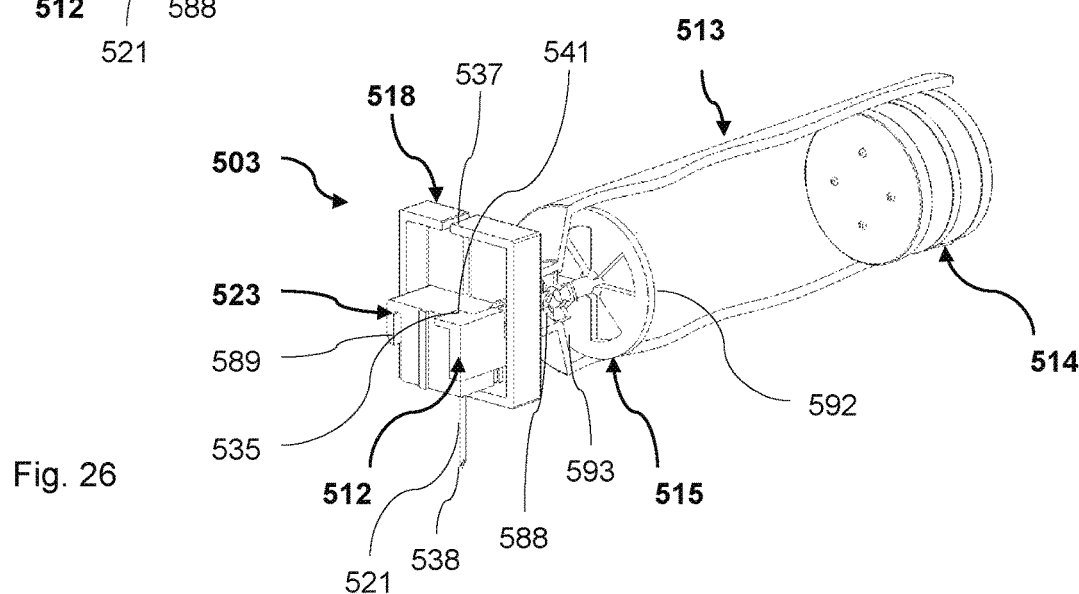
Figure 27:
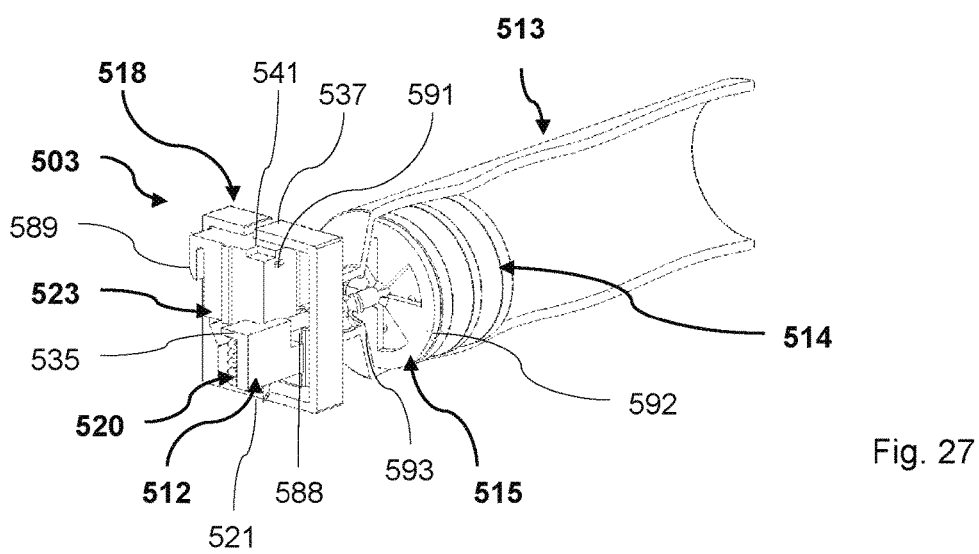

In the following, a few exemplary embodiments of the invention are described in further details with reference to the drawings, wherein FIG. 1 shows a perspective view of a device according to an embodiment of the invention, FIG. 2 shows an exploded view of a device according to an embodiment of the invention, FIG. 3 shows a perspective view of a device according to an embodiment of the invention without cover and with parts of the trigger removed and which has not yet been activated, FIG. 4 shows a perspective view of a device according to an embodiment of the invention without cover and with parts of the trigger removed and which has been activated, FIG. 5 shows a perspective view of a device according to an embodiment of the invention without cover and with parts of the trigger removed, which has been activated and where the cartridge has been moved to penetrate the needle, FIG. 6 shows a perspective view of a device according to an embodiment of the invention without cover and with parts of the trigger removed, which has fulfilled the injection and wherein the needle has been retracted, FIG. 7 shows a perspective view of a needle unit according to an embodiment of the invention with parts of the needle housing missing and which has not been activated, FIG. 8 shows a perspective view of a needle unit according to an embodiment of the invention with parts of the needle housing missing and which has been activated, FIG. 9 schematically shows a vertical sectional view of an osmotic actuator according to an embodiment of the invention, which has not yet been activated, FIG. 10 schematically shows a vertical sectional view of an osmotic actuator according to an embodiment of the invention, which has been activated and wherein the plunger has been moved the full stroke, FIG. 11 shows a perspective view of the actuator according to an embodiment of the invention, which is unpressurised before activation, FIG. 12 schematically shows a vertical sectional view of an osmotic actuator according to an embodiment of the invention, which is unpressurised before activation and which has not yet been activated, FIG. 13 schematically shows a vertical sectional view of an osmotic actuator according to an embodiment of the invention, which is unpressurised before activation, which has been activated but wherein the plunger has not yet started to move, FIG. 14 schematically shows a vertical sectional view of an osmotic actuator according to an embodiment of the invention, which is unpressurised before activation, which has been activated and wherein the plunger has been moved the full stroke, FIG. 15 shows a perspective view of a device according to an embodiment of the invention with the housing and parts of the trigger removed and with a bended plunger rod and an actuator with a bigger osmosis membrane area, which has not yet been activated, FIG. 16 shows a perspective view of a device according to an embodiment of the invention with the housing and parts of the trigger removed and with a bended plunger rod and an actuator with a bigger osmosis membrane area, which has been activated, FIG. 17 shows an exploded view of a device according to an embodiment of the invention with a bended plunger rod, and with an actuator with a bigger osmosis membrane area, FIG. 18 shows an exploded view of an actuator for a device according to an embodiment of the invention with a bigger osmosis membrane area, FIG. 19 shows a perspective view of the actuator according to an embodiment of the invention with an osmotic hollow fibre membrane unit, FIG. 20 shows a perspective view of the actuator according to an embodiment of the invention with an osmotic hollow fibre membrane unit and with parts of the actuator removed, FIG. 21 schematically shows a vertical sectional view of an osmotic actuator according to an embodiment of the invention with an osmotic hollow fibre membrane unit, which has not yet been activated, FIG. 22 schematically shows a vertical sectional view of an osmotic actuator according to an embodiment of the invention with an osmotic hollow fibre membrane unit, which has been activated and in which the plunger has reached the end position, FIG. 23 shows a perspective view of a device according to an embodiment of the invention without the upper housing and with an alternative needle assembly permanently attached to the cartridge, which has not yet been activated, FIG. 24 shows a perspective view of a device according to an embodiment of the invention without the upper housing and with an alternative needle assembly permanently attached to the cartridge, which has been activated, FIG. 25 shows a perspective view of a needle assembly according to an embodiment of the invention where the needle is retracted by means of the cartridge plunger and where the needle has not yet been inserted, FIG. 26 shows a perspective view of a needle assembly according to an embodiment of the invention where the needle is retracted by means of the cartridge plunger and where the needle has been inserted, and FIG. 27 shows a perspective view of a needle assembly according to an embodiment of the invention where the needle is retracted by means of the cartridge plunger and where the needle has been retracted.

DETAILED DESCRIPTION

In the following, the terms "up", "down", "upper", "lower", "upward", "downward", "left" and "right" refer to the drawings and do not necessarily correspond to a situation of use.

Parts, which are fixed together to form a functional unit acting as one part, might be divided in a different way, or the functional unit may form more or less parts, and this will still be within the scope of the invention as defined by the claims. The term "membrane", even if used in the singular, covers both one or more flat sheet membranes and combinations of one or more flat sheet membranes, hollow fibre membranes and other available membrane types.

In some embodiments, it is possible to use the hydraulic pressure induced in the actuator directly on the plunger in the cartridge in such a way that the solvent from the actuator moves down in the cartridge during the injection. Hereby, a rigid or flexible rod for transmitting the force is avoided. This will require that an amount equal to or higher than the volume of the cartridge pass through the forward osmosis membrane. If a gearing is required, a telescopic, bellow formed or other expanding unit can be arranged between the plunger in the cartridge and the solvent.

The described device, needle, plunger and actuator configurations do not necessarily have to be combined as described but can be set together in other suitable combinations.

FIG. 1 shows a perspective view of the wearable injector device 1 according to an embodiment of the invention. Visible are the base plate 4, the cartridge 13 containing the medical agent to be injected, the trigger 17 by which the needle 21 (see FIG. 13) is inserted in the skin of the user and the osmotic actuator is started, and the cover 5 enclosing and protecting the parts of the wearable injector device 1. The base plate 4 has an adhesive tape on its outer side to enable the injector device 1 to be attached to the skin of a user during the injection. Instead of a needle, a soft cannula or a catheter might be inserted in the skin of the user and the device might also be connected with a tube, so that a user can wear the device away from the injection site, with or without the use of adhesive tape.

FIG. 2 shows an exploded view of the wearable injector device 1. The exploded view can be referred to when the perspective and sectional views do not clearly show the details of a component. Visible in FIG. 2 are the base plate 4 with a cavity 49 for receiving a needle assembly 3 and with four snap arms 25 for locking the base plate 4 to the cover 5, the osmotic actuator 2 including a plunger 9 and a plunger extension 8 attached to and advancing the cartridge plunger 14 in the cartridge 13 during injection, the components of the needle assembly 3, the needle lock 15, the trigger 17, an actuator lock 16 holding against the osmotic pressure before the device is triggered, and the cover 5 with the opening 27 for receiving the trigger 17 and a window 26 for inspecting the content of the cartridge 13.

FIGS. 3-6 shows the different functional steps of the wearable injector device 1. FIG. 3 shows a device, which is ready to be activated by pushing the trigger 17 after the device has been attached to the skin. The actuator lock 16 is in its locking position where the locking arm 30 is engaging the slit 33 in the plunger 9 of the osmotic actuator 2 (see FIG. 2). The needle assembly 3 comprises a double-ended needle 21 with a first end adapted to penetrate the septum (not shown) of the cartridge 13, when the cartridge 13 is moved towards the needle assembly 3, and a second end adapted to be inserted in the tissue of the user (please refer to FIGS. 7 and 8 for detailed views of the needle assembly in the different operational positions).

In FIG. 4, the trigger 17 is pushed, which has pushed the actuator lock 16 to the left due to the engagement between the curved track 28 in the trigger 17 and the protrusion 29 on the actuator lock 16 and guided by the ribs 31. This has disengaged it from the slit 33 in the plunger 9 and the osmotic actuator 2 is thereby activated, but the plunger 9 and the plunger extension 8 has not yet moved. The needle assembly 3, however, has been affected, as the slanted protrusion 44 on the lower side of the trigger 17 via the rotatable arm 24 has pushed the second end 38 of the needle 21 out through an opening in the base plate 4, and the needle tip of the needle 21 is slightly visible in FIG. 4. The rotation of the rotatable arm 24 has moved a first end 41 of the rotatable arm 24 out of the opening 42 in the needle assembly 3, and the first end 41 has snapped passed the spring arm 35 on the needle lock 15 preventing it from moving back due to the spring force from the spring 20, which has been tensed during the operation.

In FIG. 5, the osmotic actuator 2 has moved the plunger 9 and the plunger extension 8 a small distance, which can easily be seen by looking at the shelf 34 on the plunger extension 8. The cartridge 13 is free to move along its centre axis and, consequently, it has been moved towards the needle assembly 3 until shortly after the first end 39 of the needle 21 has penetrated the septum (not shown) on the cartridge 13. The injector device is now in full fluid communication with the needle 21 and further movement of the plunger 9 will inject the therapeutic agent out through the needle 21 and into the tissue of the user.

In FIG. 6 the injection is fully accomplished. The plunger extension 8 with the shelf 34 has moved the full stroke of the actuator 2 guided by the track 32, which has caused the full amount of the therapeutic agent to be pushed out of the cartridge 13, through the needle and into the tissue of the user. At the end of the stroke, the shelf 34 on the plunger extension 8 has mated with the shelf 30 on the needle lock 15 and the needle lock 15 has been pushed a small distance. This has disengaged the spring arm 35 on the needle lock 15 from the first end 41 of the rotatable arm 24 of the needle assembly 3. During triggering of the device 1, the slanted protrusion 44 was pushed pass the needle assembly 3 allowing the rotatable arm to be rotated back to the initial position by the spring 20 in the end of the injection. This has in turn retracted the needle 21 to an inaccessible position within the interior of the needle assembly 3 and the wearable injector device.

FIGS. 7 and 8 display the needle assembly 3 in the retracted and the inserted positions, respectively. In FIG. 8, it is clearly seen how the first end 41 of the rotatable arm 24 is moved out of the housing 18 when the needle is inserted, to allow the second end 38 of the needle 21 to be locked in the inserted position by the needle lock 15. The embodiment shown in FIGS. 7 and 8 is slightly different from the previously described embodiment as it further has a horizontal movable part 12, which is moved by the trigger of the device, when the trigger is pushed. As the needle 21 is secured to the horizontal movable part 12, the second end 39 (see FIG. 2) of the needle 21 will thereby be pushed to penetrate the septum of the cartridge 13, and the need for the cartridge 13 to move during the initial phases of the injection cycle is thereby eliminated.

All openings in the needle assembly 3 are covered by a material capable of maintaining the needle assembly 3 sterile until the sterile barriers are broken during triggering of the device.

In the following, the function of the osmotic actuator 2 is explained with reference to FIGS. 9 and 10. FIG. 9 shows the actuator 2 comprising the actuator housing 6 and actuator lid 7, a flexible membrane 10, a strainer 53 with a semipermeable forward osmosis membrane 11 disposed on the upper side, and a plunger 9 sealed with an O-ring and movable the full stroke of the injection in a cylindrical bore in the actuator housing 6.

Next to the plunger 9, the plunger extension 8 can be seen. The function of the plunger extension 8 is to carry the plunger 14 in the cartridge 13 and to provide a moving part outside the cartridge 13 capable of making contact with and move the needle lock 15 in the end of the injection to set the needle 21 free to be retracted to a hidden position within the needle assembly 3. The actuator housing 6, the actuator lid 7, the end of the plunger 9 and the flexible membrane 10 together forms a cavity, which is divided into two chambers 45/46 by the semipermeable membrane 11. The first chamber is a low-pressure chamber 45 and it contains a solvent, preferably fresh water or deionized water, and the second chamber is a high-pressure chamber 46 containing a solution. $CaCl_2$) dissolved in fresh water is a very powerful osmotic solution but other solutions may be used.

The semipermeable forward osmosis membrane 11 is non-flexible and braced by the strainer 53. The forward osmosis membrane 11 only allows water molecules to pass but retains the majority of the salt molecules and, as the osmotic forces tries to equalize the concentration of solution in the two chambers, water will be drawn from the low-pressure chamber 45 and into the high-pressure chamber 46. This applies a force on the plunger 9, which is thereby pushed forward, and which, via the plunger extension 8, pushes the plunger 14 in the cartridge 13 forward. The push force during the injection is a result of the concentration of and the type of salt in the solution, the cross section of the plunger 9 and the ratio in volume between the two chambers 45/46, where a higher ratio ensures less dilution and a more constant force during the injection.

As water moves from the low-pressure chamber 45 to the high-pressure chamber 46, the volume of the low-pressure chamber 45 must adjust to the decreasing amount of water. This is possible by means of the flexible membrane 10 and, therefore, also the stiffness of this membrane will affect the resulting push force. Other means such as a movable plunger or a valve may be incorporated in the low-pressure chamber to prevent a loss of force due to vacuum in the low-pressure chamber 45. The time of a full stroke of the plunger 9 is dependant of the permeability and the area of the semipermeable forward osmosis membrane 11, the concentration of and the type of salt in the solution, the resistance of the plunger and O-ring and of the flexible membrane 10 and of the temperature of the solvent and solution.

In FIG. 9, the slit 33 in the plunger 9 can be seen clearly and visible is also the track 47 in the actuator housing 6. Before the osmotic actuator 2 is actuated, the plunger force is counteracted by the actuator lock 16, as explained earlier, which on the other hand is counteracted by the ribs 31 on the actuator housing 6 (see FIGS. 2-6) and the track 47, which both allows for sideward movement of the actuator lock 16 to the right.

In FIG. 10, the plunger 9 has moved the full stroke and, consequently, also the plunger extension 8 has moved in the track 32 in the actuator housing 6. Due to the movement of the plunger 9, the total volume of the second chamber 46 has increased and it is also clear that the membrane 10 has been stretched and the volume of the first chamber 45 has decreased to accommodate this.

The osmotic actuator is preferably of the disposable kind and should be disposed of after use of the device corresponding to one full cycle of sequences, but a reloadable device is, however, within the scope of the invention. In this case, the osmotic actuator should be reloaded by means of reverse osmosis, or the chambers should be emptied and refilled.

If the plunger 9 in the actuator 2 has a smaller cross-section than the plunger 14 in the cartridge 13, then a gearing is achieved and the transport of water through the forward osmosis membrane 11 will be lower than the volume of therapeutic agent to be injected.

An actuator 102, which is unpressurised until the device is actuated, is shown in FIGS. 11-14. A perspective view of the actuator 102 can be seen in FIG. 11. A syringe 154 with a plunger 160 and an empty flexible pouch 156 are tightly attached to the actuator 102. The function of these will be explained later. Also visible in FIG. 11 are the plunger 109 and the plunger extension 108 guided in the track 132 in the housing parts 106, 107 and with a shelf 134 for releasing the needle in the end of the injection.

In the following, the different stages of the actuator 102 shown in FIGS. 12-14 are explained. In FIG. 12, the actuator 102 has not yet been activated. The low-pressure chamber 145 and the high-pressure chamber 146 are both filled with a solution, and the forward osmosis membrane 111 braced by the strainer 153 separates the chambers. An activation chamber 159 in the form of a syringe 154 contains a solvent and the activation chamber 159 is separated from the low-pressure chamber 145 by a one-way valve, preferably of the duckbill type. Connected to the low-pressure chamber 145 is also an expansion chamber 156 in the form of a flexible pouch, which allows the low-pressure chamber 145 to expand in volume.

In FIG. 13, the actuator is activated and the plunger in the syringe 154 has moved and pushed the solvent through the valve 158 and into the low-pressure chamber 145. Duckbill valves have a very low opening pressure and are, consequently, very suited for the purpose, however other types of valves could be used. The solvent from the syringe has mixed with and diluted the solution in the low-pressure chamber 145 and an amount of the diluted solution has filled and expanded the expandable chamber 156. As the forward osmosis membrane 111 now has a solvent or rather a diluted solution on one side and the undiluted solution on the other side, the osmotic pressure is starting to build up, but as can be seen in the FIG. 13, the plunger 109 has not yet moved.

In FIG. 14, a large amount of the diluted solution from the low-pressure chamber 145 has moved through the forward osmosis membrane 111 and into the high-pressure chamber 146 due to osmosis and, in order to accommodate the extra volume, the plunger 109 has been pressed down. At the same time, the activation chamber 159 has been emptied. This has also pressed down the plunger extension 108 and, when the actuator 102 is built into a fully equipped device, the plunger extension 108 in turn pushes down the plunger in the cartridge to expel the content. When the plunger 109 has been pushed down a certain specified distance, the O-ring that tightens the plunger in the corresponding bore passes the by-pass channel 157 and the osmotic pressure will press the solution from the high-pressure chamber 146 back into the low-pressure chamber 145 and, after a while, the salination will be the same on both sides of the forward osmosis membrane 111 and the osmotic forces will stop, and the actuator will hereafter be unpressurised. Preferably, a one-way valve e.g. of the duckbill type is locking the flow in one direction in the channel 157, to prevent that fluid is lost from the low-pressure chamber 145 before the by-pass situation occurs.

To vary the time for a full stroke of the plunger 109, the area of the forward osmosis membrane can be varied, however if a very short injection time is desired, it might not be possible to achieve a forward osmosis membrane area big enough with the use of a normal flat sheet membrane, and in this case other membrane arrangements are preferred. These include folded membranes, winded membranes or one or more membrane tubes or cylinders arranged side by side.

In FIGS. 15-17, another embodiment of the device 201 with an alternative osmotic actuator configuration 202 is shown. FIGS. 15 and 16 show perspective views of the embodiment without the upper cover 205 before and after the user actuates the device by pushing on the trigger 217, respectively, (the trigger 217 being displayed with a cut-out in the upper surface to ease understanding), and FIG. 17 shows an exploded view of the embodiment for reference. The actuator 202 is equipped with a bellow bottle 254 forming an activation chamber 259 and containing a solvent and the activation chamber is separated from the low-pressure chamber 245 by a valve, which only allows fluid to move from the activation chamber 259 to the low-pressure chamber 245. The low-pressure chamber 245 has a flexible membrane 210 to allow it to expand when the content of the activation chamber 259 is pushed into the low-pressure chamber 245 (this will be further explained later). The plunger 269 in this embodiment moves, unlike the other embodiments, away from the needle assembly 203, and to be able to push the plunger in the cartridge 213 toward the needle assembly 203, the embodiment makes use of a flexible plunger rod 209, which is guided in a cam 264 to reverse the actuation direction. The flexible plunger rod 209 is shown as being a tightly winded spring but could also be a profile shaped sheet metal band (as used in a measuring tape) or other suitable, flexible materials or configurations. This allows the device to be much smaller and the cartridge to have a bigger volume, which are great advantages.

In FIG. 15, the device 201 is not yet triggered and the protrusion 261 on the inside of the trigger 217 has not yet pushed the bellow bottle 254 to empty the solvent into the low-pressure chamber. Similarly, the slanted protrusion 244 on the inside of the trigger 217 has not yet been pushed through the needle assembly 203 to push down the needle into the tissue of the user and the other end of the needle into the septum of the cartridge.

In FIG. 16, the trigger 217 has been pushed, and the activation chamber 259 formed by the bellow bottle 254 is compressed and the content of the activation chamber 259 is emptied into the low-pressure chamber 245. The slanted protrusion 244 on the trigger 217 has been pushed through the needle assembly 203, which has pushed down the needle into the tissue of the user and locked the needle in this position by means of the needle lock 215 (will be further described later). The other end of the needle has been pushed through the septum on the cartridge 213, and a fluid pass way has been established. The actuator is now initiated and a pressure will start to build up in a high-pressure chamber 246 of the actuator 202, which in turn will move the plunger 269 with a speed dependant of, among other things, the difference in salination and the membrane area. The flexible plunger rod 209 will now push the plunger 214 in the cartridge 213 in the opposite direction of the plunger 269 expelling the therapeutic agent out through the needle. After the content of the cartridge 213 has been almost fully expelled, the needle lock 215 is pushed away from the needle assembly 203 by the plunger 269, and after the needle lock has moved a short distance, the needle is released and will be retracted to a hidden position inside the device 201.

An exploded view of the actuator is shown in FIG. 18. In this embodiment, the activation chamber 259 containing the solvent is formed by the interior of the bellow bottle 254, and the low-pressure 245 and the high-pressure 246 chambers are arranged on top of each other with the high-pressure chamber 246 below. Before the device is actuated, both of the low-pressure 245 and the high-pressure 246 chambers are filled with a solution. Between the low-pressure and the high-pressure chambers a rigid strainer 211 with multiple holes is arranged with the forward osmosis membrane 253 on the lower side heading towards the high-pressure chamber 246. The activation chamber 259 formed by the bellow bottle 254 is locked to the actuator via the opening 265 in the housing parts 206/207 and it is in fluid communication with the third chamber 259 via the pass way 267, though restricted by the duckbill valve which requires a specific pressure to open. The flexible membrane 210 allows the low-pressure chamber 245 to vary the volume. To activate the actuator 202 the content of the activation chamber 259 is emptied into the low-pressure chamber 245 through the one-way duckbill valve 258 by a push on the bellow bottle 254. This causes the flexible membrane 210 to bulge and the low-pressure chamber 245 to expand in volume. The content of the activation chamber 259 is hereby mixed with the content of the low-pressure chamber 245, whereby the low-pressure chamber ends up with a solution with a lower concentration then the solution in the high-pressure chamber 246. Due to the difference in salination water molecules from the low-pressure chamber 245 move to the high-pressure chamber 246, and a pressure starts to build up in the high-pressure chamber 246. This pressure exerts a force on the plunger 269 (see FIG. 17) in the cylindrical opening 266 in the lower actuator housing 207 and consequently the plunger 269 and the plunger rod 209 (see FIG. 17) is moved. When the plunger 269 has been moved the desired distance, it will pass the bypass hole formed by the holes 257a/257b in the upper 206 and lower 207 actuator housing parts and the pressure difference between the low-pressure 245 and the high-pressure 146 chambers is equalized.

An embodiment 301 having a larger membrane area is shown in FIGS. 19-22. As can be seen in FIG. 20, a membrane unit 380 is composed by a number of hollow fibre membranes 381 and two end caps 387, and the hollow fibres 381 are open in one end and closed in the other end. Thereby, a considerable larger membrane surface area can be provided compared with a device using a flat sheet, and it is easy to vary the number of hollow fibres 381 according to the desired injection time. Another advantage is that the hollow fibres are self-supporting, whereby a separate support for the membranes so that they can withstand the pressure in the actuator is avoided. The membrane unit 380 is arranged tightly in an end-housing 306, which is welded to a main-housing 307 such that the open end 385 of the hollow fibres 381 is pointing towards the low-pressure chamber 345 and such that the membrane unit 380 is separating the low-pressure 345 and high-pressure 346 chambers. In some embodiments, the membrane unit 380 is open in both ends and arranged in such a way that both ends are open into the same or into two different low-pressure chambers 345, as this can make it easier to prevent air in the fibres and to fill the membrane unit.

A cylindrical bore 382 with a first movable plunger 309 is in fluid communication with the high-pressure chamber 346, and a second movable plunger 378 is arranged in the low-pressure chamber 345, which is formed by a cylindrical portion 379 of the end-housing 306, so that both the low-pressure and the high-pressure chambers can change volume when the solvent in the low-pressure chamber moves through the hollow fibres 381 and into the high-pressure chamber.

Another difference from the previous described embodiments is that, instead of injecting a solvent such as deionized water to the low-pressure chamber 345 to mix with and dilute a solution, salt crystals are added to the high-pressure chamber 346, which in turn contains a solvent. The salt crystals 386, preferably magnesium chloride or sodium chloride but other salts may also be used, are arranged in a syringe housing (activation chamber) 376 with a foil 384 or other kind of tight connection closing the one end and a plunger rod 377 closing the other end. In some embodiments, a valve, a shutter or a movable shield is used to separate the high-pressure chamber 346 and the activation chamber 376 before the device is activated. The advantage by using salt crystals 386 instead of a salt solution is that the resulting solution, after the salt crystals 386 has been moved into the high-pressure chamber 346, can be oversaturated to prevent the solution from being diluted during the osmotic process. However, in some embodiments of the actuator it might be seen as an advantage to use a salt solution instead of salt crystals.

In the following, the function of this embodiment is described with reference to FIGS. 21 and 22. In FIG. 20, the actuator is not yet actuated and both the low-pressure chamber 345 and the high-pressure chamber 346 are filled with a solvent. The first plunger 309 is in the initial position and have not yet moved the flexible plunger rod (not shown) and the second plunger 378 is in an extreme position allowing enough room for the initial amount of solvent. The salt crystals are shielded from the high-pressure chamber 346 by the foil 384.

In FIG. 22, the plunger rod 377 is pushed by the trigger in the device (not shown), which in turn has penetrated the foil 384 and moved the salt crystals 386 into the high-pressure chamber 346 where it has been dissolved in the solvent. As this has caused a difference in salination between the two chambers, the solvent has been drawn though the hollow osmosis membrane fibres 381 of the membrane unit 309, which again has moved the first and the second plunger 309 to the end positions. Preferably a shortcut between the low-pressure and high-pressure chambers is created at the end of the required movement of the first plunger, to ensure that the actuator 301 stops working and is without pressure.

If the fibres have a large diameter, it is possible to turn around the osmosis direction and to have high pressure inside the fibres 381 and low pressure outside the fibres. This requires that the salt/salt solution is released inside the fibre (or rather cylinder) or fibres when the device is activated, and in this case it would be beneficial that the low-pressure chamber 345b is formed by a bag or flexible foil, which can be adapted to fill up available space in the device very efficiently.

FIGS. 23 and 24 show another embodiment of the needle assembly 403, in which the needle assembly 403 together with the cartridge 413 forms a sterile unit. In FIG. 23, a wearable injection device with the needle assembly 403 is showed. For the sake of clearness, the trigger and the upper housing are removed. The needle assembly comprises a needle 421 with a sharpened needle end 438 for penetrating the skin of the user (see FIG. 24), a sterile barrier in the form of a bellow 474 closed in one end and a coil spring (not visible) inside the bellow and between the lower housing 404 and the needle assembly 403. The needle 421 is either insert moulded, glued or by other means fixed to a needle connector 424, which comprises a first end 472 that forms a cavity for connecting tightly to the cartridge 413 e.g. of the Luer taper fitting type but other types of bacteria tight connections may be used, and a second end 473 movable relative to the first end and connected with and guiding the sharpened needle end 438. The two needle ends 472, 473 are connected via an intermediate flexible part 471 through which there is a fluid pass way from the cartridge 413 to the sharpened needle end 438. The needle 421 can either follow the entire length of the needle, the needle connector 424 can be hollow or the two ends 472, 473 of the needle connector 424 can be connected via a tube or the like. If the cartridge 413 has a septum that must be penetrated, a sharpened needle end may be provided in the first needle connector end 472 as well.

A pin 475 on the lower housing 404 guides the second needle connector end 473 in the up and down movement via a hole in the second needle connector end and ensures that the sharpened needle end 438 moves straight up and down, however this feature can be left out if it is considered acceptable that the needle 421 follows a circular path during the insertion. In this case the intermediate part 471 of the needle connector 424 does not have to be flexible.

In the following, the different operational stages of the needle assembly 403 are explained. In FIG. 23, the device 401 is ready for use but the trigger (not shown) has not yet been pushed. The needle assembly 403 is tightly and bacteria tight secured to the cartridge and the needle assembly 403 and cartridge 413 together forms a sterile cavity. The bellow barrier 474 has not yet been compressed and the sharpened needle end 438 (see FIG. 24) has not yet been pushed out through the opening in the lower housing 404.

In FIG. 24, the trigger has been pushed and this has pushed the second needle end 473 of the needle connector 424 down and compressed the bellow formed sterile barrier 474 and the coil spring inside (not visible), and thereby exposed the needle 421 through an opening in the lower housing 404. During this the first connector end 472 has been rotated and the cartridge has been rotated as well, and it is also clear that the flexible intermediate part 471 has been bended to allow the sharpened needle end 438 to move straight down. The second needle end 473 of the needle connector 424 is locked in position by the spring arm 435 on the needle lock 415 and, at the end of the injection cycle, the actuator will move the needle lock 415 a small distance until it is free of the needle assembly 403, after which the coil spring (not visible) will move the second connector end 473 up and thereby retract the sharpened needle end 438 to an inaccessible position. As the needle lock 415 is moved by the plunger in the actuator 402, the sharpened needle end 438 might be retracted during the last part of the injection, in which case the remaining therapeutic agent will be collected in the bellow formed sterile barrier 474.

In another embodiment of the needle assembly 403, the cartridge 413 and the needle assembly 401 do not rotate when the wearable injection device 401 is activated. In this embodiment, the second needle end 473 simply moves up and down relative to the first needle end 472 and guided by the pin 475 when the device is triggered, which in turn will allow the needle assembly 403 to be smaller and take up less space. At the same time, this will bend the intermediate part 471 of the needle connector 424 more than what is the case in the first embodiment. FIGS. 25-27 show an embodiment of the needle assembly 503 with an inlet needle 588 for connecting to the cartridge 513 and an outlet needle 521 with a sharpened end 538 (see FIG. 26) to be inserted in the subject to be injected, in which the two needles 588, 521 are disconnected until the device is activated. The inlet needle 588 is inserted in a horizontally moving part 512 with a hole in the side (not visible) or they are moulded as one part, and the outlet needle 521 is inserted in a vertically moving part 523 with a hole 541 in the side, and after activation of the device, the two holes are aligned to provide a fluid communication between the inlet needle 588 and the outlet needle 521. Another characteristic of this embodiment is that the outlet needle 521 is released in the end of the injection by means of the plunger 514 and a release item 515 in the cartridge 513. The release item 515 comprises a front part 593 positioned in the proximal end of the cartridge 513 with a little diameter and a back part 592 positioned in the main part of the cartridge 513 with a bigger diameter and the release part is capable of moving a few millimetres along the axis of the cartridge. In an alternative embodiment, the release item is fixed to and moves with the cartridge plunger 514 and is having a shape suited therefore. The figures are shown with parts of the housing removed to ease the understanding of the movements of the parts.

In FIG. 25, the needle assembly 503 is in the initial state and the wearable injection device has not yet been activated. The vertically moving part 523 is in the upper position biased by the spring 520 and the needle 521 is hidden inside the needle assembly housing 518, and the horizontally moving part 512 is in a position where the main body of the part is protruding out of the needle assembly housing while the needle 588 is hidden inside the needle assembly housing 518. The plunger 514 is in the initial position and the release item 515 is in a retracted position.

In FIG. 26, the vertically moving part 523 has been pressed down to a position where the outlet needle 521 is protruding out of the housing 518 by means of a first protrusion (not shown) e.g. on a trigger, which has been moved through the slit 537 in the needle assembly housing 518, and the spring 520 has been compressed. Before the first protrusion has been moved past the vertically moving part 523, the horizontal moving part 512 has been pushed by a second protrusion (not shown) e.g. on the trigger which in turn has pushed the inlet needle 588 through the septum on the cartridge 513 to a position where the needle tip is lying at or near the front part 593 of the release item, and the shelf 535 on the horizontally moving part 512 is now lying in the cut-out 541 on the vertically moving part 523 and preventing the part from moving up due to the spring 520. The hole 541 in the vertically moving part 523 is now aligned with the hole (not visible) in the horizontally moving part 512, and a fluid communication is established. The flexible arm 589 on the vertically moving part 523 is cooperating with geometry in the housing 518 in pressing the vertical and horizontally moving parts against each other and securing a tight connection between the two movable parts.

In FIG. 27, the injection is at or near the end and the plunger 514 has moved to the proximal end of the cartridge 513. This has pushed the release item 515 a few millimetres which in turn has pushed the horizontal moving part 512 a few millimetres, which again has released the vertically moving part 523. Hereafter, it is moved up by the spring 520 and the outlet needle 521 is retracted to a hidden position. All openings in the needle assembly 503 are covered by a material capable of maintaining the needle assembly 503 sterile until the sterile barriers are broken during triggering of the device.

The invention claimed is:

1. A wearable injection device, comprising:
   a cartridge with a septum and a movable plunger, the plunger movable along a longitudinal axis of the cartridge and the cartridge containing a therapeutic agent to be injected, and
   a needle assembly, the needle assembly comprising:
   a first part and a needle, the needle held by the first part and the needle configured to penetrate an injection site on the skin of a user, and the first part and the needle movable in a first direction that is mainly perpendicular to the longitudinal axis of the cartridge,
   a second part and a penetrating portion, the penetrating portion held by the second part and the penetrating portion configured to penetrate the septum of the cartridge, and the second part and the penetrating portion movable in a second direction that is along the longitudinal axis of the cartridge, and
   a spring that biases the first part toward an initial position in which the needle is hidden within the wearable injection device,
   wherein, during activation of the device:

the first part with the needle is moved in the first direction against the biasing of the spring to an inserted position in which the needle penetrates the injection site; and the second part is moved in the second direction so that the penetrating portion penetrates the septum of the cartridge, and a locking portion of the second part engages a portion of the first part to preclude movement of the first part in a direction opposite to the first direction so that the second part locks the first part in the inserted position with the needle penetrated into the injection site, wherein a fluid communication between the first part and the second part is established simultaneous with or after the locking of the first part in the inserted position, and wherein movement of the moveable plunger injects the therapeutic agent out through the needle into the user, and wherein the second part is moved in a direction opposite to the second direction by the movable plunger near an end of an injection of the therapeutic agent so that the locking portion disengages the first part and the first part is released from the inserted position and moved back toward the initial position by the spring.

* * * * *